US005824700A

United States Patent [19]
Frydman et al.

[11] Patent Number: 5,824,700
[45] Date of Patent: Oct. 20, 1998

[54] ORTHO-QUINONE DERIVATIVES NOVEL SYNTHESIS THEREFOR AND THEIR USE IN THE INHIBITION OF NEOPLASTIC CELL GROWTH

[75] Inventors: Benjamin J. Frydman; Donald T. Witiak; Jerry Shunneng Sun; Andrew H. Geiser, all of Madison, Wis.

[73] Assignee: Wisconsin Alumni Research Foundation, Madison, Wis.

[21] Appl. No.: 604,131

[22] Filed: Feb. 20, 1996

[51] Int. Cl.$^6$ .......................... A61K 31/35; C07D 311/92
[52] U.S. Cl. .......................... 514/454; 549/389; 549/458
[58] Field of Search .................................. 549/389, 458, 549/454

[56] References Cited

U.S. PATENT DOCUMENTS 4,778,805  10/1988  Adams et al. .
5,244,917   9/1993  Petraitis et al. .

FOREIGN PATENT DOCUMENTS

WO-A-
9404145  3/1994  WIPO .

OTHER PUBLICATIONS

Cooke, R.G., Dunnione and Related Naphthoquinones, *Australian J. of Scient. Res.* (1950) CA) 3, 481–96.

Cooke, Raymond G., Raston, Colin L., and White, Allan H., Crystal Structure of Dunnione p–Bromophenylhydrazone, *Aust. J. Chem.*, (1980), 33, 441–5.

Inoue, Kenichiro; Ueda, Shinichi; Nayeshiro, Hidekazu; and Inouye, Hiroyuki, Structures of Unusually Prenylated Naphthoquinones of *Streptocarpus dunni* and its Cell Cultures, *Chem. Pharm. Bull.*, (1982) 30(6), 2265–8.

Inoue, Kenichiro; Ueda, Shinichi, Nayeshiro, Hidekazu; and Inouye, Hiroyuki, Quinones of *Streptocarpus dunnii*, *Phytochemistry*, (1983) 22(3), 737–41.

Inoue, Kenichiro; Ueda, Shinichi; Nayeshiro, Hidekazu; Moritome, Nobuharu; and Inouye, Hiroyuki, Biosynthesis of Naphthoquinones and Anthraquinones in *Streptcarpus dunnii* Cell Cultures, *Phytochemistry*, (1984) 23(2), 313–18.

Planchon, Sarah M.; Wuerzberger, Shelly; Frydman, Benjamin; Witiak, Donald T.; Hutson, Paul; Church, Dawn R.; Wilding, George; and Boothman, David A., βLapachone–mediated Apoptosis in Human Promyelocytic Leukemia (HL–60) and Human Prostate Cancer Cells: A p53–independent Response, *Cancer Research*, (1995) 55, 3706–11.

Rüedi, Peter and Hans Eugster, Conrad, Isolation of (–) dunnione from the leaves of *Calceolaria integrifolia*, *Helvectia Chimica Acta.*, vol. 60, Fasc. 3 (1977)—Nr. 96, 945–47.

Mock et al., "Chemical studies of the proteaceae". Aust. J. Chem. 26, 1121–30, 1973.

Schaffner–Sabba et al., "Beta–Lapachone: Synthesis of derivatives and activities in tumor models". J. Med. Chem. 27, 990–994, 1984.

Goncalves et al., "Evaluation of the toxicity of 3–allyl–beta–lapachone against Trypanosoma Cruzi bloodstream forms." Mol. Biochem. Parasit. vol. 1, 167–176, 1980.

Lopes et al., "In vitro in vivo evaluation of the toxicity of 1,4–naphthoquinone and 1,2–naphthoquinone derivatives against Trypanosoma Cruzi". Ann. Trop. Med. Parasit. vol. 72(6), 523–531, 1978.

*Chemical Abstracts* (1989), vol. 110, No. 1, p. 35, Abstract No. 88167h, Boothman et al., Inhibition of Potentially Lethal DNA Damage Repair in Human Tumor Cells by Beta–Lapachone, see abstract & *Cancer Research* (1989), vol. 49, No. 3, pp. 605–612, ENGL.

*Chemical Abstracts* (1979), vol. 94, No. 1, p. 25, Docampo et al., Beta–Lapachone Enhancement of Lipid Peroxydation, Abstract No. 151101p, see abstract & *Biochem. Pharmacol.* (1979), vol. 28, No.6, pp. 723–728, ENGL.

*Chemical Abstracts* (1990), vol. 112, No. 21, Boothman, D., Can A DNA Repair Inhibitor Block the Tumorigenic Transformation of Normal Cells Following a Genetic Insult?, Abstract No. 30301x, see abstract & *Biol. Zentralblat.* (1989), vol. 108, No. 5, pp. 415–421, ENGL.

*Chemical Abstracts* (1995), vol. 122, No. 25, p. 460, Szumiel et al., Effects of Topoisomerase I–Targeted Drugs on Radiation Response of L5178Y, Abstract No. 309888w, see abstract & *Int. J. Radiat. Biol.* (1995), vol. 67, No. 4, pp. 441–448, ENGL.

*Chemical Abstracts* (1995), vol. 123, No. 1, p. 43, Planchon et al., Beta–Lapachone Mediated Apoptosis in Human Promyelocytic Leukemia (HL–60) and Human Prostate Cancer Cells, Abstract No. 217883h, see abstract & *Cancer Research* (1995), vol. 55, No. 17, pp. 3706–3711, ENGL.

*Chemical Abstracts* (1995), vol. 123, No. 1, p. 43, Chiang Li et al., Induction of Apoptosis by Beta–Lapachone in Human Prostate Cancer Cells, Abstract No. 217884j, see abstract & *Cancer Research* (1995), vol. 55, No. 17, pp. 3712–3715, ENGL.

(List continued on next page.)

*Primary Examiner*—José G. Dees
*Assistant Examiner*—Barbara Badio
*Attorney, Agent, or Firm*—DeWitt Ross & Stevens SC

[57] ABSTRACT

The invention relates to β-lapachone derivatives of formula II and compositions containing said compounds:

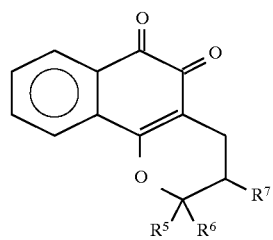

Formula II wherein, $R^5$, $R^6$ and $R^7$ are as defined in the specification. The compounds are potent inhibitors of neoplastic cell growth and proliferation.

7 Claims, 10 Drawing Sheets

OTHER PUBLICATIONS

Boothman et al., Inhibition of Radiation Induced Neoplastic Transformation by Beta–Lapachone, *Proceedings of the National Academy of Sciences, USA* (Jul. 1989), vol. 86, No. 13, pp. 4963–4967.

*Chemistry Abstracts* (1973), vol. 78, No. 27, p. 361, Mock et al. Chem., Studies of the Proteaceae VI, Abstract No. 147733k, see abstract & *Aust J. Chem.* (1973), vol. 26, No. 5, pp. 1121–1130, Sydney.

*Chemical Abstracts* (1977), vol. 87, No. 17, p. 58, Pinto et al., Schstosoma Mansoniblockage of Cercarial Skin Penetration by Chemical Agents. I., Abstract No. 127264r, see abstract & *Trans. R. Soc. Trop. Med. Hyg.* (1977), vol. 71, No. 2, pp. 133–135, Brazil.

ORTHO-QUINONE DERIVATIVES NOVEL SYNTHESIS THEREFOR AND THEIR USE IN THE INHIBITION OF NEOPLASTIC CELL GROWTH

FIELD OF THE INVENTION

This invention is directed to novel o-quinone and o-naphthoquinone derivatives which are structurally related to naturally-occurring lapachones and dunniones. The present invention is also drawn to a novel synthetic method to produce tricyclic derivatives, including lapachone and dunnione, as well as the use of these compounds in the inhibition of neoplastic cell growth.

DESCRIPTION OF THE PRIOR ART

The present invention is drawn toward novel tricyclic naphthoquinone derivatives, a synthetic method for making the derivatives, and use of the derivatives to inhibit neoplastic cell proliferation. The naphthoquinone derivatives of the present invention are related to the compounds known by their trivial names as β-lapachone (1) (7,8-dihydro-2,2-dimethyl-2H-naphtho(2,3-b)dihydropyran-7,8-dione) and dunnione (2) (2,3,3-trimethyl-2,3,4,5-tetrahydro-naphtho(2,3-b)dihydrofuran-6,7-dione).

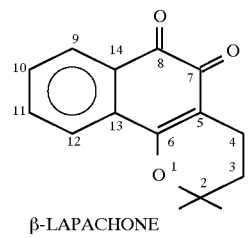

β-LAPACHONE

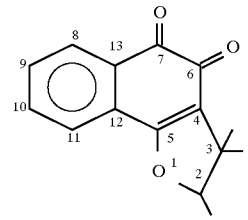

DUNNIONE

β-lapachone is a naturally occurring product which can be found in small amounts in the lapacho tree (*Tabebuia avellanedae*) of South America. β-Lapachone may also be readily synthesized from lapachol (3), an abundant quinone which is also found in the lapacho tree.

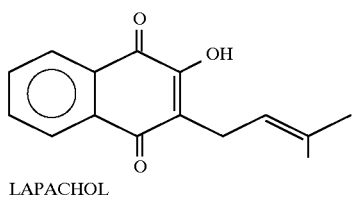

LAPACHOL

In similar fashion, dunnione (2) and its structural isomer α-dunnione (2a) (2,2,3-trimethyl-2,3,4,5-tetrahydro-naphtho(2,3-b)dihydro-furan-6,7-dione) can be isolated from the leaves of *Streptocarpus dunnii*.

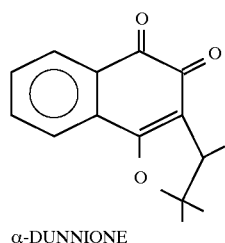

α-DUNNIONE

Early work on the synthesis of these related naphthodihydrofurandiones and naphthodihydropyrandiones began with Fieser's 1927 synthesis of lapachol (3) (Fieser, L. F. (1927), *J.A.C.S.*, 49: 857.) The first known synthesis of dunniones (2 and 2a) and related naphthoquinones was performed by R. G. Cooke and co-workers at the University of Melbourne using a modification of Fieser's above-noted synthesis. (Cooke, R. G. et al. (1950), *Australian J. of Scient. Res.*, 3:481–94.) In short, the Fieser method synthesizes β-lapachol (3) via alkylation of the silver salt of lawsone (i.e., 2-hydroxy-1,4-naphthoquinone) with dimethylallyl bromide in absolute ether. This synthetic route yields both the C-alkylated product (lapachol), as well as an O-alkylated by-product.

Cooke et al. modified this general procedure by beginning with the potassium salt of lawsone rather than the silver salt. The C-alkylated product (lapachol) is separated from the O-alkylated intermediate by acidification, which precipitates the lapachol from solution.

What is left behind is an O-alkylated lawsone derivative, namely, 2-(3',3'-dimethylalloxy)-1,4-naphthoquinone (4):

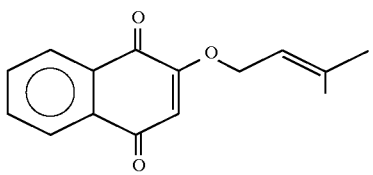

Compound (4) is then subjected to a Claisen rearrangement by refluxing in absolute ethanol to yield 2-hydroxy-3-(1',1'-dimethylallyl)-1,4-naphthoquinone (5):

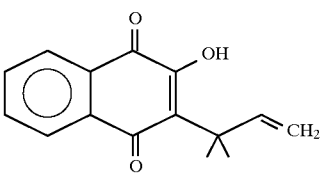

Under these mild conditions, Cooke et al. report that the conversion of (4) to (5) is practically quantitative. However, under more rigorous conditions, mixtures of the 1,2-dimethylallyl and 2,3-dimethylallyl isomers are also found.

Treatment of compound (5) with concentrated sulfuric acid yields a 2-ethyl-2-methyl derivative of dunnione (6):

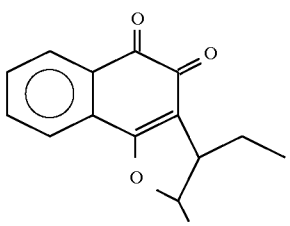

In an interesting aside, Professor Cooke appears to have maintained a life-long interest in the dunniones as evidenced by his 1980 paper "Crystal Structure of Dunnione p-Bromophenylhydrazone," which was published 30 years after the above-described reference. (*Aust. J. Chem.* (1980), 33:442–5.)

A group of researchers led by Kenichiro Inoue has published several articles discussing the structure and biosynthetic pathways of various naphthoquinones isolated from *S. dunnii*. For instance, in a communication to the editor, Inoue et al. report the structure of several prenylated naphthoquinones from *S. dunnii*. In addition to dunnione, this reference also describes the isolation and characterization of 7-hydroxydunnione, 8-hydroxydunnione, and dehydrodunnione. This reference also describes the 1,4-naphthoquinone isomer of α-dunnione. This reference is limited solely to isolating the above-noted compounds from cell cultures of *S. dunnii*. A full-length paper describing the isolation and characterization of these naphthoquinones can be found in a 1983 publication of Inoue et al. (*Phytochemistry* (1983), 22(3):737–741.)

In a follow-up paper (*Phytochemistry* (1984), 23(2):313–318) Inoue et al. report a radioisotopic study to determine the biosynthetic pathways of several naphthoquinones and anthroquinones isolated from *S. dunnii*. Inoue et al. performed this study by inserting $^{13}$C- and $^{2}$H-labeled precursors into cell cultures of *S. dunnii*. The fate of the isotopically-labeled precursors was then tracked. Inoue et al. conclude that all of the dunnione naphthoquinone derivatives are biosynthesized via a common 4-(2'-carboxyphenol)-4-oxobutanoic acid precursor. This reference describes the formation of the deuterated 2-prenyl ether of lawsone by reacting lawsone with dimethylallyl bromide in the presence of potassium carbonate. Both deuterated lawsone and the deuterated 2-prenyl ether of lawsone were then administered to cell cultures of *S. dunnii* to determine the intermediacy of lawsone in the synthesis of dunnione. It must be noted, however, that this reference is silent regarding artificial methods for synthesizing dunnione and dunnione derivatives. Rather, Inoue et al. are limited to a discussion regarding possible biological pathways for the synthesis of naphthoquinones and anthraquinones in *S. dunnii*.

A German-language reference to Rüedi and Eugster describes the isolation of partially racemic (−)-dunnione from *Calceolaria integrifolia*. (Rüedi and Eugster (1977), *Hel. Chim. Acta*, 60(3) 96: 945–947.) According to the authors, this appears to be the first record of the occurrence of dunnione outside the family Gesneriaceae. In Gesneriaceae, dunnione is usually found as the dextrorotary enantiomer.

While dunniones, lapachones, and several derivatives thereof have been described in the prior art, no biological utility has been described in any of the above references, nor has any direct utility been described for any of the above-noted naphthofurandione or naphthopyrandione derivatives.

In the patent literature, Adams et al., U.S. Pat. No. 4,778,805, describe 4,7-benzofurandione derivatives which are useful as inhibitors of leukotriene synthesis. Because the benzofurandiones described by Adams et al. tend to inhibit mammalian leukotriene biosynthesis, they are described as useful therapeutic agents for treating allergic conditions, asthma, psoriasis, and other maladies which are biologically mediated by various leukotrienes.

Petraitis et al., U.S. Pat. No. 5,244,917, describe a large number of substituted naphthofurans which find use as anti-inflammatory agents.

None of the above references, taken alone or in any combination, are seen as describing the presently disclosed invention.

SUMMARY OF THE INVENTION

One aspect of the present invention is directed to a novel method to synthesize tricyclic o-naphthoquinones. The method is directed to synthesizing compounds of Formula I or II:

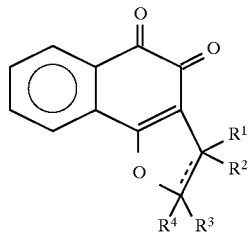

Formula I

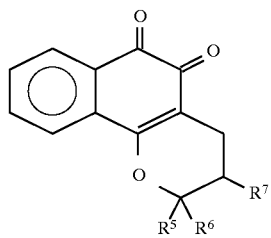

Formula II wherein $R^1$-$R^6$ are each, independently, selected from the group consisting of H, $C_1$–$C_6$ alkyl, $C_1$–$C_6$ alkenyl, $C_1$–$C_6$ alkoxy, $C_1$–$C_6$ alkoxycarbonyl, —$(CH_2)_n$-aryl, —$(CH_2)_n$-heteroaryl, —$(CH_2)_n$-heterocycle, and —$(CH_2)_n$-phenyl; or $R_1$ and $R^2$ combined are a single substituent selected from the above group, and $R^3$ and $R^4$ combined are a single substituent selected from the above group, in which case—is a double bond; and $R^7$ is H, OH, $C_{1-C_6}$ alkyl, $C_{1-C_6}$ alkenyl, $C_{1-C_6}$ alkoxy, $C_1$–$C_6$ alkoxycarbonyl, —$(CH_2)_n$-amino, —$(CH_2)_n$-aryl, —$(CH_2)_n$-heteroaryl, —$(CH_2)_n$-heterocycle, or —$(CH_2)_n$-phenyl, wherein n is an integer of from 0 to 10.

The method includes the steps of alkylating a Group IA metal salt of lawsone with an allyl halide of the formula:

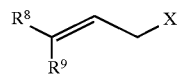

in the presence of M-I; wherein $R^8$ and $R^9$ are each, independently, selected from the group consisting of H, $C_1$–$C_6$ alkyl, $C_1$–$C_6$ alkenyl, $C_1$–$C_6$ alkoxy, $C_1$–$C_6$ alkoxycarbonyl, —$(CH_2)_n$—aryl, —$(CH_2)_n$-heteroaryl, —$(CH_2)_n$-phenyl; and X is a halide, and M is a Group IA metal; which yields a mixture of C-alkylated and O-alkylated lawsone derivatives.

The mixture of C-alkylated and O-alkylated lawsone derivatives is then cyclized to yield a tricyclic ortho-naphthoquinone.

The present invention is further drawn to a method of synthesizing compounds of Formula I or II:

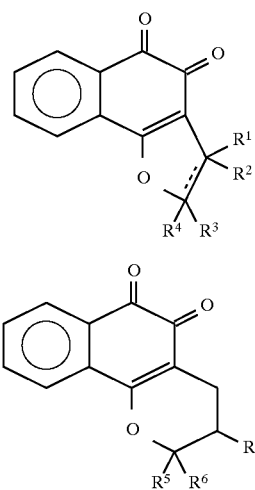

Formula I

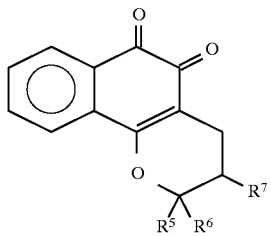

Formula II wherein $R^1$-$R^6$ are each, independently, selected from the group consisting of H, $C_1$–$C_6$ alkyl, $C_1$–$C_6$ alkenyl, $C_1$–$C_6$ alkoxy, $C_1$–$C_6$ alkoxycarbonyl, —$(CH_2)_n$-aryl, —$(CH_2)_n$-heteroaryl, —$(CH_2)_n$-heterocycle, and —$(CH_2)_n$-phenyl; or $R^1$ and $R^2$ combined are a single substituent selected from the above group, and $R^3$ and $R^4$ combined are a single substituent selected from the above group, in which case—is a double bond; and $R^7$ is H, OH, $C_1$–$C_6$ alkyl, $C_1$–$C_6$ alkenyl, $C_1$–$C_6$ alkoxy, $C_1$–$C_6$ alkoxycarbonyl, —$(CH_2)_n$-amino, —$(CH_2)_n$-aryl, —$(CH_2)_n$-heteroaryl, —$(CH_2)_n$-heterocycle, or —$(CH_2)_n$-phenyl; and n is an integer of from 0 to 10.

The synthetic method includes the steps of synthesizing a lithium salt of lawsone by contacting lawsone at a temperature equal to or less than about −78° C. with lithium hydride. Whereby the lithium salt is afforded.

The lithium salt of lawsone is then alkylated with an allyl halide of the formula:

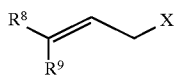

in the presence of M-I, wherein $R^8$ and $R^9$ are each, independently, selected from the group consisting of H, $C_1$–$C_6$ alkyl, $C_1$–$C_6$ alkenyl, $C_1$–$C_6$ alkoxy, $C_1$–$C_6$ alkoxycarbonyl, —$(CH_2)_n$-aryl, —$(CH_2)_n$-heteroaryl, —$(CH_2)_n$-heterocycle, and —$(CH_2)_n$-phenyl; X is a halide, and M is a Group IA metal, which yields a mixture of C-alkylated and O-alkylated lawsone derivatives.

The mixture of C-alkylated and O-alkylated lawsone derivatives is then separated from one another to yield a first portion of C-alkylated derivatives and a portion of O-alkylated derivatives. The portion of O-alkylated lawsone derivatives is then rearranged to yield a second portion of C-alkylated lawsone derivatives. The first and second portions of C-alkylated lawsone derivatives are cyclized to yield a tricyclic ortho-naphthoquinone.

Using the synthetic method described above, several novel compounds have been synthesized. Among these compounds are compounds selected from the group consisting of Formula I or II:

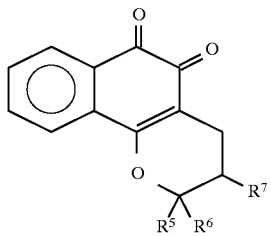

Formula I

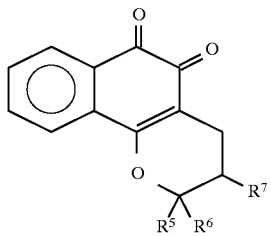

Formula II wherein $R^1$–$R^6$ are each, independently, selected from the group consisting of H, $C_1$–$C_6$ alkyl, $C_1$–$C_6$ alkenyl, $C_1$–$C_6$ alkoxy, $C_1$–$C_6$ alkoxycarbonyl, —$(CH_2)_n$-aryl, —$(CH_2)_n$-heteroaryl, —$(CH_2)_n$-heterocycle, and —$(CH_2)_n$-phenyl; or $R^1$ and $R^2$ combined are a single substituent selected from the above group, and $R^3$ and $R^4$ combined are a single substituent selected from the above group, in which case—is a double bond: and $R^7$ is H, OH, $C_1$–$C_6$ alkyl, $C_1$–$C_6$ alkenyl, $C_1$–$C_6$ alkoxy, $C_1$–$C_6$ alkoxycarbonyl, —$(CH_2)_n$-amino, —$(CH_2)_n$-aryl, —$(CH_2)_n$-heteroaryl, —$(CH_2)_n$-heterocycle, or —$(CH_2)_n$-phenyl, and n is an integer of from 0 to 10, and salts thereof; except when $R^1$, $R^2$, $R^3$, $R^5$ and $R^6$ are methyl, then $R^4$ and $R^7$ are substituents other than hydrogen; and when $R^2$, $R^3$ and $R^4$ are methyl, then $R^1$ is a substituent other than hydrogen.

A distinct advantage of the present synthetic method is that it allows for the synthesis of novel o-naphthoquinone derivatives, including lapachone and dunnione derivatives, using lawsone as a starting material. Lawsone is a commodity chemical which can be readily purchased in large quantities. This is a vast improvement over isolation of these products from natural sources or synthesis from naturally-occurring precursors.

The presently described synthetic method is also remarkably efficient and clean. The overall synthesis yields dunnione, lapachone, and other tricyclic o-naphthoquinone derivatives in heretofore unattainable yields and purity.

The synthesis is also quite easy, thereby avoiding the cumbersome manipulations required in prior art synthetic methods.

Of equal importance, the biological activity of the compounds described herein is remarkable in that the compounds are potent inhibitors of neoplastic cell growth and proliferation. The compounds described herein find use as chemotherapeutic agents in the treatment of a wide range of neoplasms, including cancers of the prostate, breast, colon, and lung. The compounds exhibit their anti-proliferative effects in heretofore unknown, minute concentrations.

In light of the newly-discovered biological activity of these compounds, another aspect of the present invention is drawn to a method of inhibiting growth of cancer cells by contacting the cells with one or more compounds described herein. More specifically, this aspect of the present invention is drawn to a method of inhibiting growth of a cancer cell which comprises contacting the cancer cell with an effective growth-inhibiting amount of a compound selected from the group consisting of 4-($C_1$–$C_6$ alkoxy)-1,2-naphthoquinones, 4-($C_1$–$C_6$ alkenyloxy)-1,2-naphthoquinones, 4-($C_1$–$C_6$ carbonyloxy)-1,2-naphthoquinones, 4-($C_1$-$C_6$ aryloxy)-1,2-naphthoquinones, 4-($C_1$-$C_6$ heteroaryloxy)-1,2-naphthoquinones, 4-(benzyloxy)-1,2-naphthoquinone, 4-($C_3$-$C_6$ cycloaryloxy)-1,2-naphthoquinones, 4-($C_3$-$C_6$ heterocycloaryloxy)-1,2-naphthoquinones, a compound of Formula I or II:

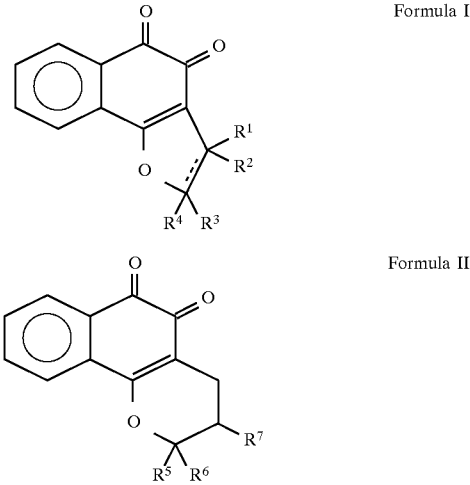

Formula I

Formula II wherein $R^1$-$R^6$ are each, independently, selected from the group consisting of H, $C_1$-$C_6$ alkyl, $C_1$-$C_6$ alkenyl, $C_1$-$C_6$ alkoxy, $C_1$-$C_6$ alkoxycarbonyl, —$(CH_2)_n$-aryl, —$(CH_2)_n$-heteroaryl, —$(CH_2)_n$-heterocycle, and —$(CH_2)_n$-phenyl; or $R^1$ and $R^2$ combined are a single substituent selected from the above group, and $R^3$ and $R^4$ combined are a single substituent selected from the above group, in which case—is a double bond; $R^7$ is H, OH, $C_1$-$C_6$ alkyl, $C_1$-$C_6$ alkenyl, $C_1$-$C_6$ alkoxy, $C_1$-$C_6$ alkoxycarbonyl, —$(CH_2)_n$-amino, —$(CH_2)_n$-aryl, —$(CH_2)_n$-heteroaryl, —$(CH_2)_n$-heterocycle or —$(CH_2)_n$-phenyl, and wherein n is an integer of from 0 to 10; pharmaceutically-suitable salts thereof, and combinations thereof.

The method includes administering to a human cancer patient in need thereof an amount of one or more of the above-described compounds which is effective to inhibit the growth of the cancer cell.

The present method for the inhibition of neoplastic cell growth has both in vivo and in vitro applications. In vivo, the method encompasses the therapeutic treatment of neoplastic growths in mammals, including humans. The treatment includes administering an effective cancer cell growth-inhibiting amount of a compound as described above to a person or animal in need thereof. In vitro, the method for neoplastic cell growth inhibition is effective for inhibiting the proliferation of a large number of different human cancer cell lines, including breast cancer, lung cancer, colon cancer, and prostate cancer.

The present invention is also drawn to a pharmaceutical unit dosage form which comprises an amount of a compound selected from the group consisting of 4-($C_1$-$C_6$ alkoxy)-1,2-naphthoquinones, 4-($C_1$-$C_6$ alkenyloxy)-1,2-naphthoquinones, 4-($C_1$-$C_6$ carbonyloxy)-1,2-naphthoquinones, 4-($C_1$-$C_6$ aryloxy)-1,2-naphthoquinones, 4-($C_1$-$C_6$ heteroaryloxy)-1,2-naphthoquinones, 4-(benzyloxy)-1,2-naphthoquinone, 4-($C_3$-$C_6$ cycloaryloxy)-1,2-naphthoquinones, 4-($C_3$-$C_6$ heterocycloaryloxy)-1,2-naphthoquinones, a compound of Formula I or II:

wherein $R^1$-$R^6$ are each, independently, selected from the group consisting of H, $C_1$-$C_6$ alkyl, $C_1$-$C_6$ alkenyl, $C_1$-$C_6$ alkoxy, $C_1$-$C_6$ alkoxycarbonyl, —$(CH_2)_n$-aryl, —$(CH_2)_n$-heteroaryl, —$(CH_2)_n$-heterocycle, and —$(CH_2)_n$-phenyl; or $R^1$ and $R^2$ combined are a single substituent selected from the above group, and $R^3$ and $R^4$ combined are a single substituent selected from the above group, in which case—is a double bond; $R^7$ is H, OH, $C_1$-$C_6$ alkyl, $C_1$-$C_6$ alkenyl, $C_1$-$C_6$ alkoxy, $C_1$-$C_6$ alkoxycarbonyl, —$(CH_2)_n$-amino, —$(CH_2)_n$-aryl, —$(CH_2)_n$-heteroaryl, —$(CH_2)_n$-heterocycle, or —$(CH_2)_n$-phenyl, and wherein n is an integer of from 0 to 10; pharmaceutically-suitable salts thereof, and combinations thereof; wherein the amount is effective to inhibit growth of cancer cells in a human cancer patient following administration thereto.

In light of the above discussion, a principal aim of the present invention is to provide novel compounds and pharmaceutical compositions which inhibit the growth of cancer cells both in vitro and in vivo at very low dosages.

It is further an aim of the present invention to provide novel synthetic methods for making the compounds described herein. Specifically, it is an aim of the present invention to provide a novel synthetic methodology for the manufacture of o-naphthoquinone derivatives, including tricyclic o-naphthofurandione and o-naphthopyrandione derivatives.

Another aim of the present invention is to provide novel pharmaceutical unit dosage forms containing naphthoquinone derivatives which inhibit the growth of cancer cells when administered to mammals in need thereof, including human cancer patients in need thereof.

Further aims, objects, and advantages of the presently described synthetic methods and products will become clear upon a complete reading of the following Detailed Description, drawings, and attached claims.

DETAILED DESCRIPTION OF THE INVENTION

Figure 1:
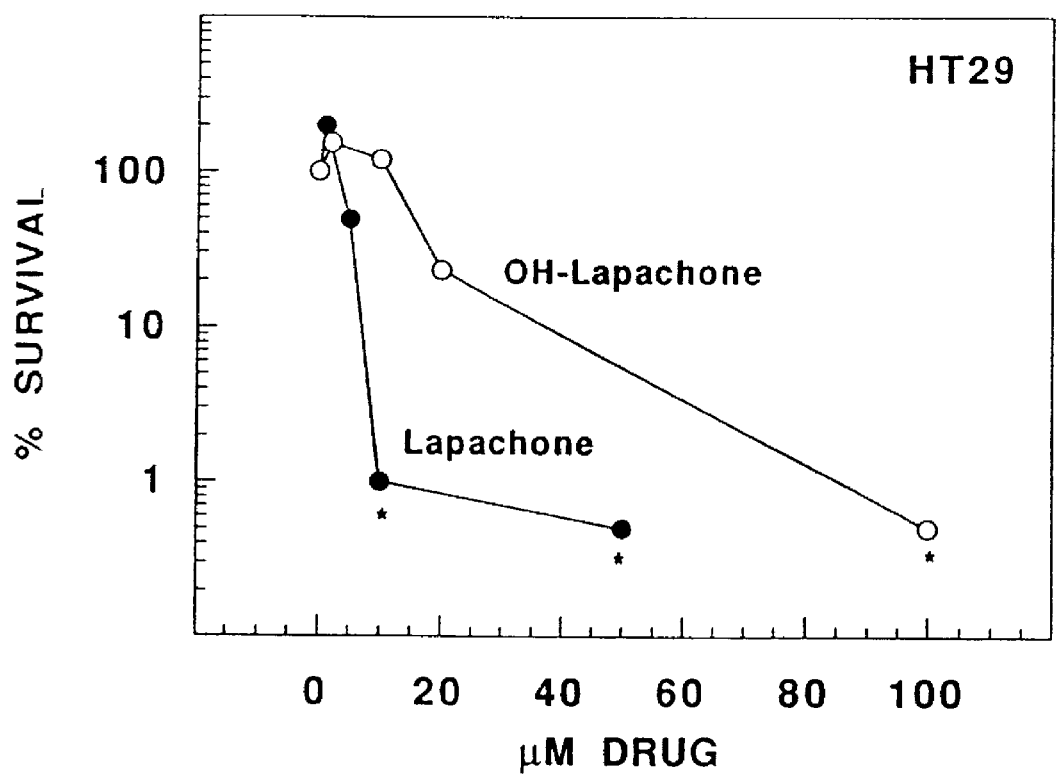
FIG. 1 is a semi-log graph depicting the fraction of cell survival in the presence of β-lapachone and 3-hydroxy-β-lapachone of colon cancer cells HT29.

The compounds described herein may be prepared using the reactions, techniques, and general synthetic procedures described herein below. Each of the references cited below are hereby incorporated herein by reference. The various reactions may be performed in various solvents which are appropriate to the reagents and materials employed and which are suitable for the transformation being effected. It is understood by those skilled in the art of organic synthesis that the functionality present on portions of a given molecule must be compatible with the reagents and reaction conditions proposed.

The synthetic method described herein generally and preferably uses lawsone (2-hydroxy-1,4-naphthoquinone) as a starting reagent. Lawsone is a commodity chemical which can be purchased in kilogram quantities from several commercial suppliers. (For instance, the Aldrich Chemical Co., Inc., Milwaukee, Wis.)

One aspect of the present invention is drawn to a preparative-scale alkylation of a Group IA metal salt of lawsone (2-hydroxy-1,4-naphthoquinone) with allyl halides to yield tricyclic ortho-naphthoquinones. As described in full, below, the resultant tricyclic o-naphthoquinones are potent inhibitors of neoplastic cell proliferation and growth. Consequently, the compounds described herein are useful in the therapeutic treatment of cancerous tumors and other neoplasms.

Preparative Alkylation of Lawsone

Alkylation of a Group IA metal salt of lawsone (i.e., lithium lawsone, sodium lawsone, potassium lawsone, etc.) with an allyl halide yields a mixture of C-alkylated products and O-alkylated products. The present synthetic method utilizes these two intermediate products to synthesize tricyclic o-naphthoquinone products such as β-lapachone, dunnione, α-dunnione, and related derivatives. The present inventors have discovered that these compounds are potent inhibitors of neoplastic cell growth and proliferation.

Reaction I illustrates the initial synthesis of the lawsone salt, followed by reaction with an allyl halide. For clarity and brevity, the remainder of the Detailed Description shall refer to the preferred embodiment of the synthesis, wherein the lawsone salt is a lithium salt and the allyl halide is an allyl bromide. This is for sake of clarity only. The presently described synthetic method functions with equal success using other Group IA metal salts of lawsone and other allyl halides, such as allyl chlorides.

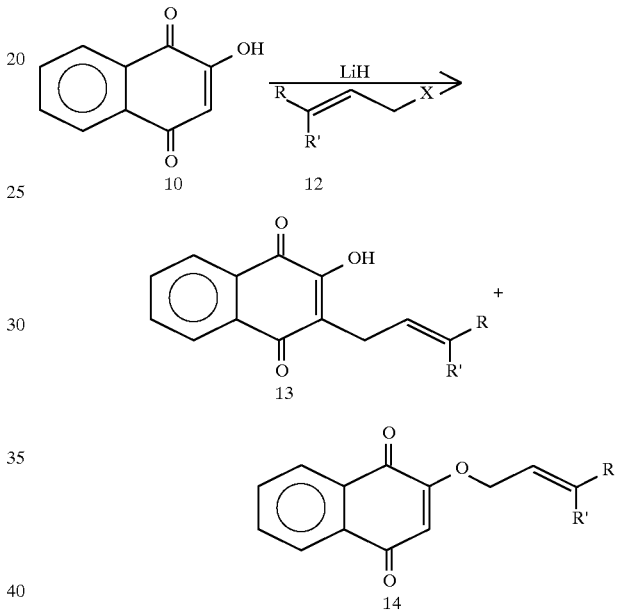

With reference to Reaction I, preferably, a lithium salt of lawsone is prepared by dissolving lawsone (10) in a suitable solvent, preferably dimethylsulfoxide (DMSO), and then adding lithium hydride, LiH. A novel and preferred protocol is to cool the lawsone solution to −78° C. prior to the addition of the LiH, and then add the LiH to the solidified reaction mixture. The solution is then slowly warmed to room temperature. As the solution warms, the LiH is slowly dissolved into the reaction mixture allowing for easy control of the evolution of hydrogen. The controlled evolution of hydrogen also eliminates the need to purge oxygen from the reaction solution by bubbling with a non-reactive gas. This makes generation of the lithium salt and the subsequent alkylation less cumbersome than prior art methods.

Alkylation proceeds by the addition of an allyl halide, preferably an allyl bromide (12) and a Group IA metal iodide, M-I, wherein M is a Group IA metal (preferably lithium), to the reaction mixture. Addition of the metal iodide serves to transform the allyl bromide in situ into an allyl iodide, which then reacts with the lawsone salt.

This in situ generation of an allyl iodide is another novel feature of the present invention. Allyl iodides are much more reactive than allyl bromides or allyl chlorides and are therefore desirable for use in alkylations. However, allyl iodides are also unstable and have a short shelf-life.

Therefore, rather than working directly with the unstable allyl iodide, the allyl iodide is generated in situ, where it reacts with the lawsone salt. In addition, the high reactivity of the allyl iodide so formed increases the overall yield of the synthesis.

As shown Reaction I, R and R' are, independently, H, $C_1$–$C_6$ alkyl, $C_1$–$C_6$ alkenyl, $C_1$–$C_6$ alkoxy, $C_1$–$C_6$ alkoxycarbonyl, —$(CH_2)_n$-aryl, —$(CH_2)_n$-heteroaryl, —$(CH_2)_n$-heterocycle, or —$(CH_2)_n$-phenyl, or $R^1$ and $R^2$ combined are H, and $R^3$ and $R^4$ combined are H, in which case—is a double bond: and $R^7$ is H, $C_1$–$C_6$ alkyl, $C_1$–$C_6$ alkenyl, $C_1$–$C_6$ alkoxy, $C_1$–$C_6$ alkoxycarbonyl, —$(CH_2)_n$-aryl, —$(CH_2)_n$-heteroaryl, —$(CH_2)_n$-heterocycle, or —$(CH_2)_n$-phenyl, wherein n is an integer of from 0 to 10.

Reaction I yields a mixture of C-alkylated lawsone derivatives (13), O-alkylated derivatives (14), and unreacted lawsone (10).

The O-alkylated derivatives (14) precipitate from solution and can be separated by filtration, centrifugation, or any other suitable means for separating solids from a reaction solution. The unreacted lawsone and the C-alkylated derivatives (13) may then be isolated based upon differences in their respective acidities by any number of well known means.

Illustratively, the reaction mixture containing lawsone and C-alkylated derivatives (13) is acidified and extracted into ethyl acetate. The lawsone is then re-extracted into a sodium bicarbonate solution (~5%) and recovered by acidification. The less basic C-alkylated derivatives are recovered from the organic solvent by extraction with sodium hydroxide (~2N) and recovered by acidification.

Overall yield is approximately 40% for the C-alkyl derivatives and approximately 30% for the O-alkyl derivatives.

REACTION II

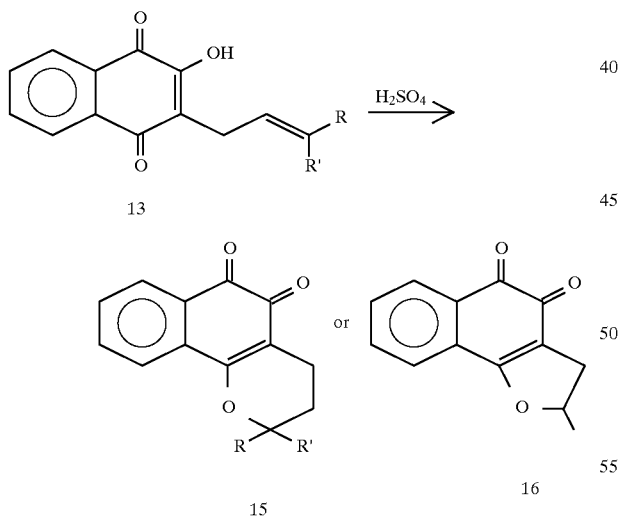

As shown in Reaction II, the C-alkylated naphthoquinone derivatives (13) can be converted into tricyclic o-naphthoquinone products via cyclization by treatment with concentrated sulfuric acid using well established procedures. (See, for instance, S. C. Hooker (1892), *J. Chem. Soc.*, 61:611.) When R and/or R' are substituents other than hydrogen, the six-membered dihydro-naphthopyrandione derivatives (15) are formed. Presumably, this arises due to stabilization of the carbocation of the secondary or tertiary carbon center. If R and R' are both hydrogen, five-membered dihydro-naphthodihydrofurandiones (16) are obtained.

Reaction III shows a Claisen rearrangement of the O-alkylated derivatives (14) to yield a rearranged intermediate (17). As depicted, the rearrangement is accomplished by refluxing in toluene (although any suitable solvent will suffice). The Claisen rearrangement is well known to synthetic organic chemists. See, for instance, R. G. Cooke, *Australian J. Sci. Res.*, above. In the same fashion as Reaction II, the rearranged product (17) of Reaction III may be cyclized by treatment with concentrated sulfuric acid.

REACTION III

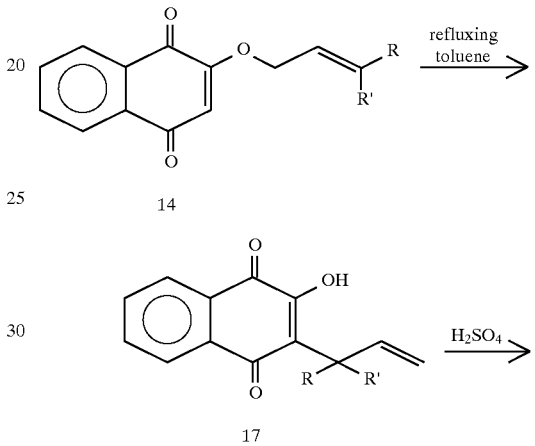

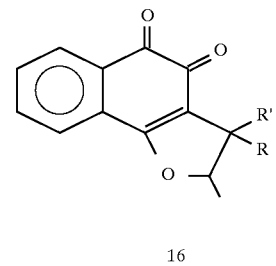

Additional derivatives of the above-described tricyclic o-naphthoquinone compounds can also be synthesized by modifying the synthetic pathway used to cyclize the third fused ring. An illustrative example, depicting the synthesis of 3-hydroxy-β-lapachone (19) is shown in Reaction IV, below:

REACTION IV

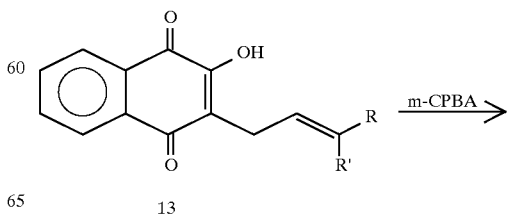

-continued
REACTION IV

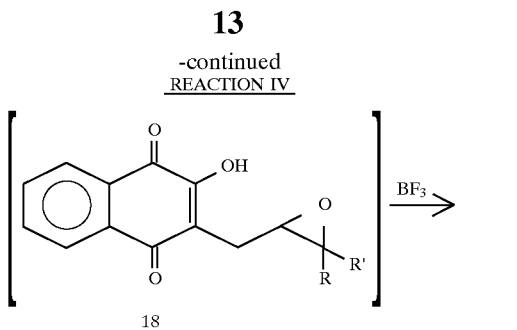

18

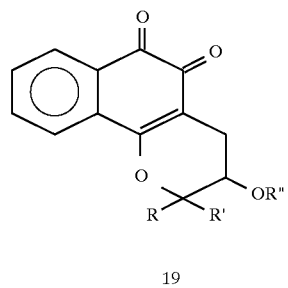

19

Here, an allyl derivative of lawsone, depicted in Reaction IV as lapachol (13) (wherein R and R' are methyl), is treated with m-chloroperoxybenzoic acid to afford the epoxide (18). Preferably, the epoxide is not isolated. Rather, the epoxide is directly transformed into the tricyclic o-naphthoquinone derivative (19) by treatment with boron trifluoride. The overall yield of product (19) is approximately 50%.

The reaction illustrated in Reaction IV is a distinct improvement over prior art ring-closure transformations leading from (13) to (19) because it is far less cumbersome. The intermediate need not be isolated and the yield is quite high.

Still other tricyclic o-naphthoquinone derivatives can be synthesized via the reaction depicted in Reaction V. Here, a fully aromatic derivative. 3,3-DINOR-2,3-dehydrodunnione, is synthesized.

REACTION V

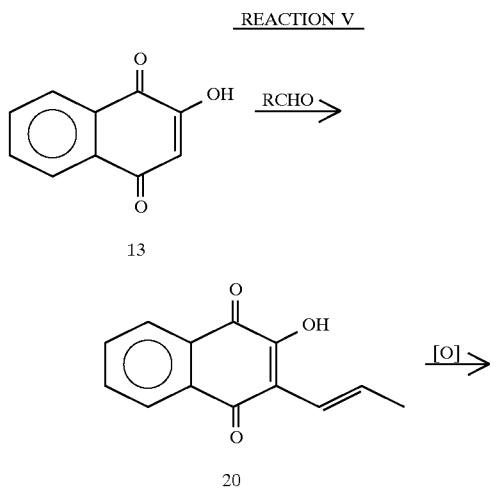

-continued
REACTION V

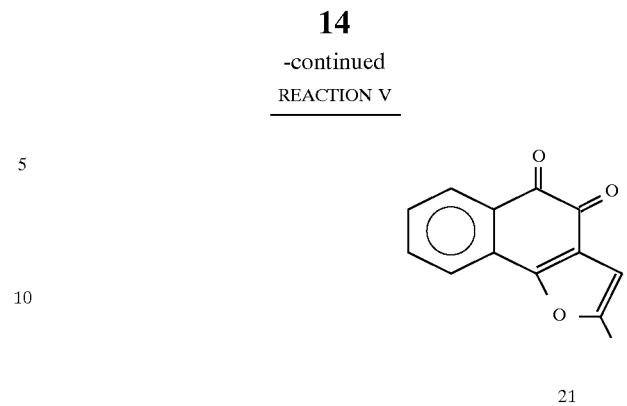

21

Here, lawsone is reacted with an aldehyde, such as propionaldehyde to yield a vinyl-p-quinone (20). The aldehyde may be selected from a wide range of suitable aldehydes and may contain additional functionalities. Suitable aldehydes include $C_1$–$C_6$ linear or branched aliphatic aldehydes, as well as $C_1$–$C_6$ dicarbonyl, cyclic, heterocyclic, aromatic, and heteroaromatic aldehydes. Cyclization of (20) under acid catalysis and mild oxidation yields the fully-aromatic dunnione derivative (21). Illustratively, the ring closure in Reaction V can be accomplished by treatment of (20) with mercuric acetate ($Hg(CH_3CO_2)_2$, a mild oxidant) in the presence of acetic acid.

The 3-hydroxy-naphtho(2,3-b)dihydropyran-7,8-dione derivatives (19) (wherein R" is hydrogen), shown in Reaction IV, can be further derivatized to hydrophobic, cationic, and anionic ortho-naphthoquinones by reaction with monoacids, amino acids, or di-acids, as shown in Reactions VI, VII, and VIII, respectively.

REACTION VI

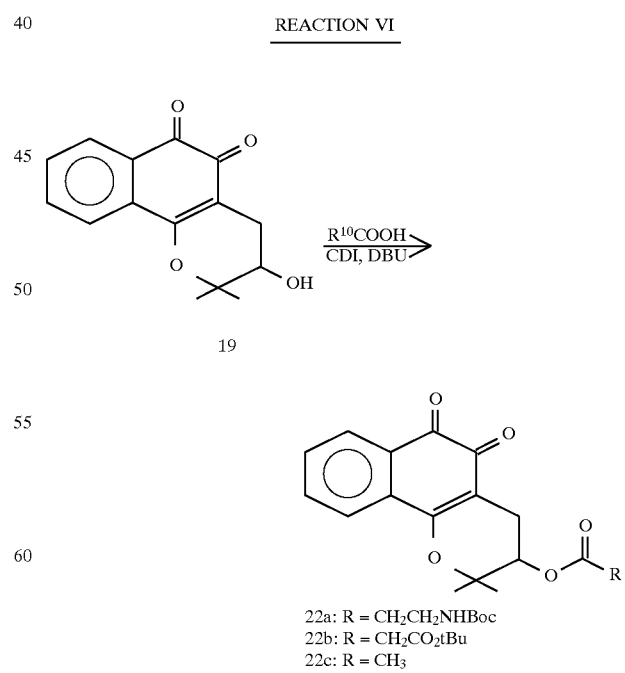

22a: R = CH₂CH₂NHBoc
22b: R = CH₂CO₂tBu
22c: R = CH₃

-continued
REACTION VII

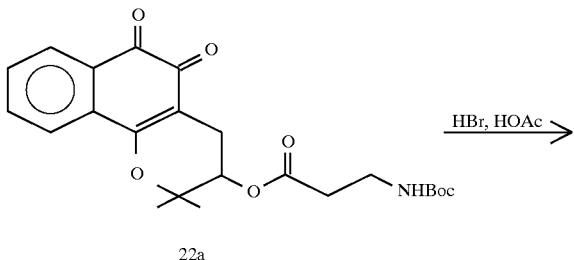

22a

REACTION VIII

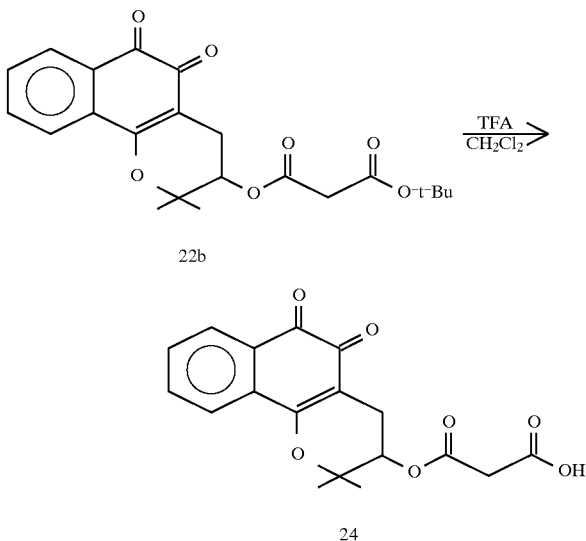

Reaction VI depicts the synthesis of mono-acid derivatives, such as the 3-O-acetyl derivative (22c). Reaction VII illustrates the synthesis of amino acid ester derivatives, such as the 3-O-alanyl derivative (23). Reaction VIII shows the synthesis of di-acid derivatives, such as the 3-O-malonyl derivative (24).

The preferred method to accomplish the transformation shown in Reaction VI is to react the 3-hydroxy-β-lapachone with an acid, $R^{10}COOH$, and the corresponding carbonyldiimidazole, CDI, in the presence of a non-nucleophilic base. As illustrated here, DBU (i.e., 1,8-diazabicyclo(5.4.0)undec-7-ene) is used. DBU is preferred. However, several equivalent reagents are known to those skilled in the art. Reaction VI can be used to generate, inter alia, carbonyl and di-carbonyl derivatives.

Reaction VII illustrates the conversion of a monoacid formed in Reaction VI into an amino acid derivative. As shown, the conversion to an amino acid salt is accomplished by treatment with HBr in a suitable solvent (e.g., diethyl ether).

Reaction VIII illustrates the synthesis of a di-acid derivative by treating a t-butyl ester generated in Reaction VI with a strong acid.

Examples and a further description of Reaction VI, VII, and VIII are included in the Examples section, below.

Biological Activity of the Tricyclic o-Naphthoquinones

Of great significance in the present invention is the utility of the described naphthoquinones to inhibit the growth and proliferation of neoplastic cells. Further still, in standard in vitro testing, the naphthoquinones described herein induce cell death in several neoplastic cell lines at drug concentrations smaller than 10 $\mu$M. The tricyclic naphthoquinones of the present invention have been shown to cause cell death in accepted in vitro test cultures for human breast cancer, lung cancer, colon cancer, and prostate cancer at minute concentrations heretofore undescribed in the scientific literature.

FIGS. 1–8 illustrate a series of experiments designed to illustrate the ability of the subject o-naphthoquinones to induce cell death in standard neoplastic cell lines. Each graph has as its X-axis the concentration of the particular compound being tested. The Y-axis of each graph is a semi-logarithmic scale of at least 4 orders of magnitude representing the fraction of cell survival in each of the cultures tested. A standardized protocol was used throughout all of the test cultures. The test protocol and neoplastic cell lines tested, as well as a complete description of each of the graphs shown in FIGS. 1–8 follows:

Cell Culture and Drug Testing Protocol

For each of the in vitro tests whose results are depicted in FIGS. 1–8, the following protocol was followed.

Day 1:

10 standard culture flasks for each drug to be tested are plated with 5×10⁵ cells in 5 mL of media and allowed to incubate for 16–24 hours at 37° C.

Day 2:

Fresh stocks of the compounds to be evaluated are prepared in sterile DMSO. For each drug, two of the ten culture flasks prepared on Day 1 are used as controls. The control flasks are treated with DMSO only. Four flasks for each compound are then treated with serially-diluted concentrations of the compound (1, 5, 10, 50 $\mu$m or 2, 10, 20, 100 $\mu$m). The remaining flasks are left untouched. The cells are incubated for 4 hours at 37° C.

After 4 hours the control flasks are counted (2 counts for each flask) and the cells per mL calculated based on the average of the control counts. The cells are then replated into six 60 mm dishes for each flask from dilutions based on the cells/mL of the control. (In the various test runs, cell concentrations ranged from approximately 50 to approximately 800 cells per mL.) Day 15–20:

The cells are monitored for colony formation. When visible, the cells are stained with 0.5% crystal violet (in 95% EtOH) and counted. The plating efficiency for each dish is then calculated. The plating efficiencies of the six dishes for each flask are averaged and the standard deviation is calculated. The fraction of cell survival at each concentration is determined based on the controls and plotted as log fraction of cell survival±standard deviation versus the dose of the compound.

Figure 2:
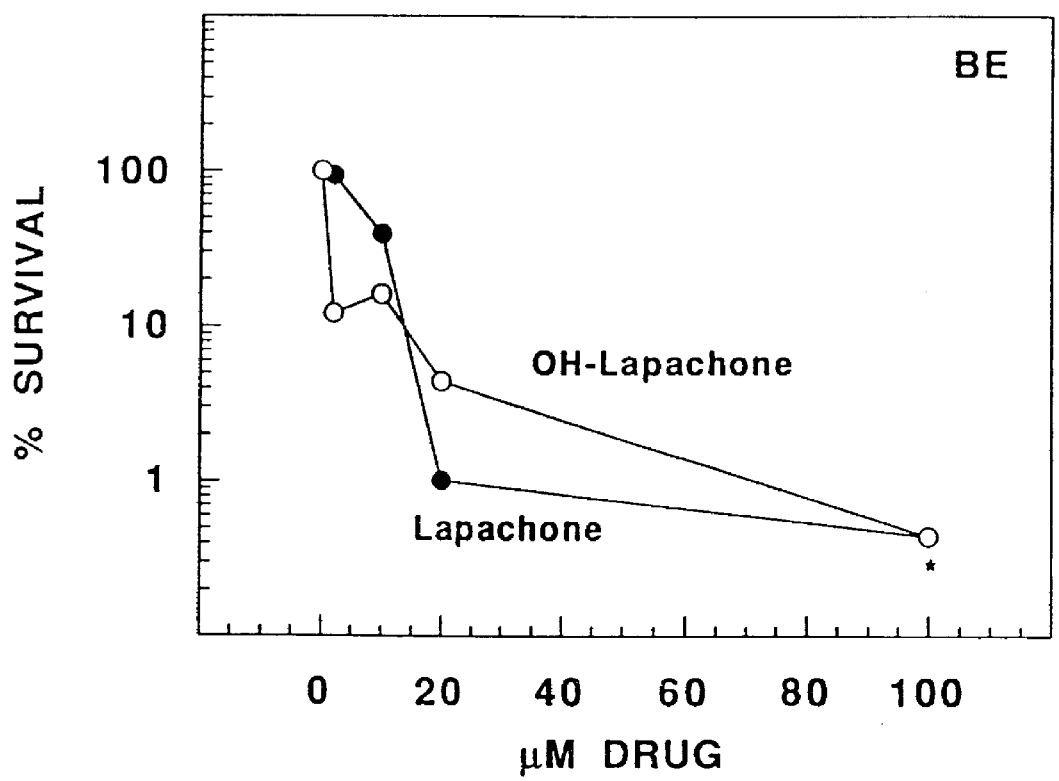
FIG. 2 is a semi-log graph depicting the fraction of cell survival in the presence of β-lapachone and 3-hydroxy-β-lapachone of colon cancer cells BE.
Figure 3:
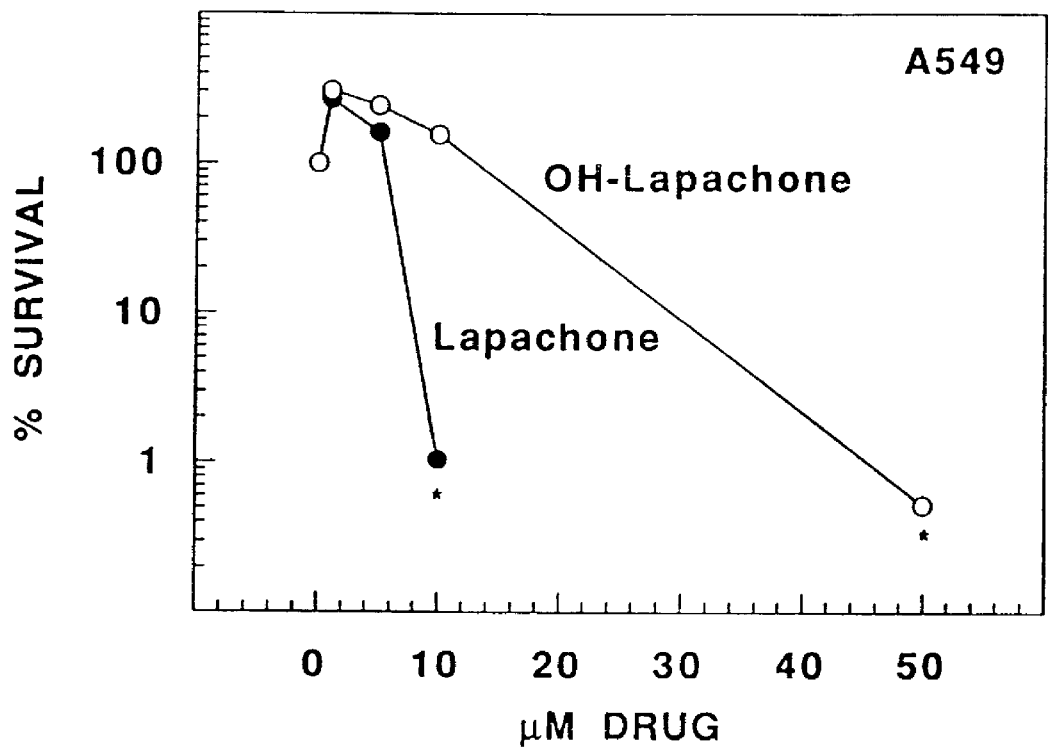
FIG. 3 is a semi-log graph depicting the fraction of cell survival in the presence of β-lapachone and 3-hydroxy-β-lapachone of lung cancer cells A549.
Figure 4:
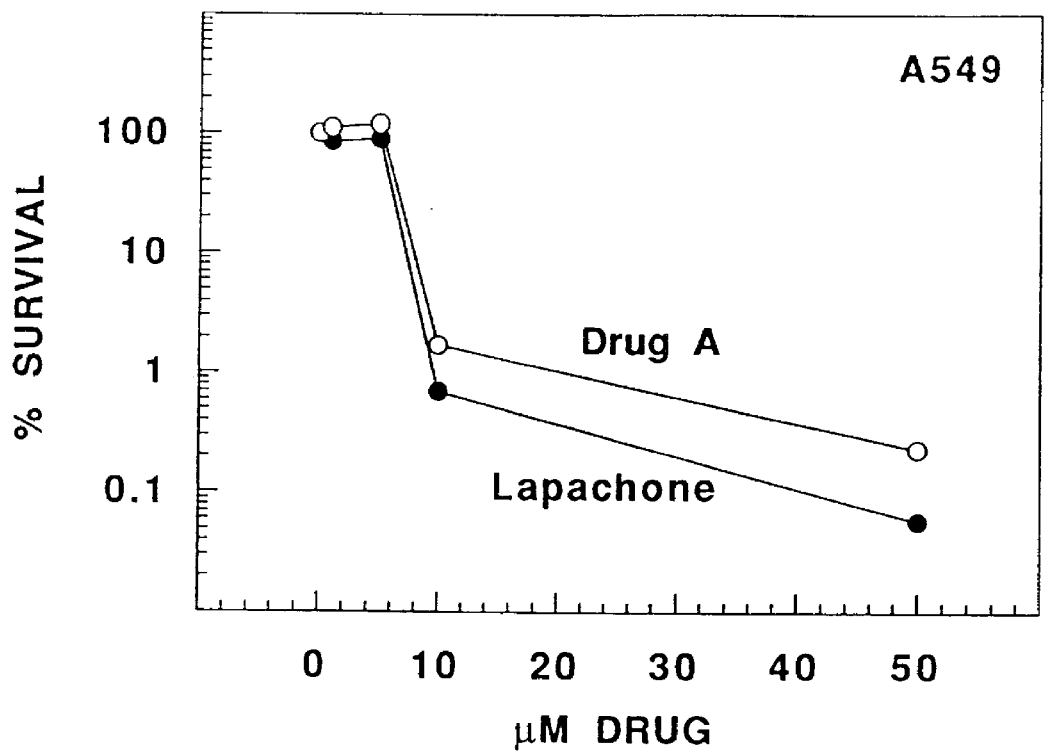
FIG. 4 is a semi-log graph depicting the fraction of cell survival of A549 lung cancer cells in the presence of β-lapachone and 2-methyl-2,3,4,5-tetrahydro-naphtho(2,3-b) dihydrofuran-6,7-dione (also called 3,3-DINOR-dunnione), designated in the graph as "Drug A."
Figure 5:
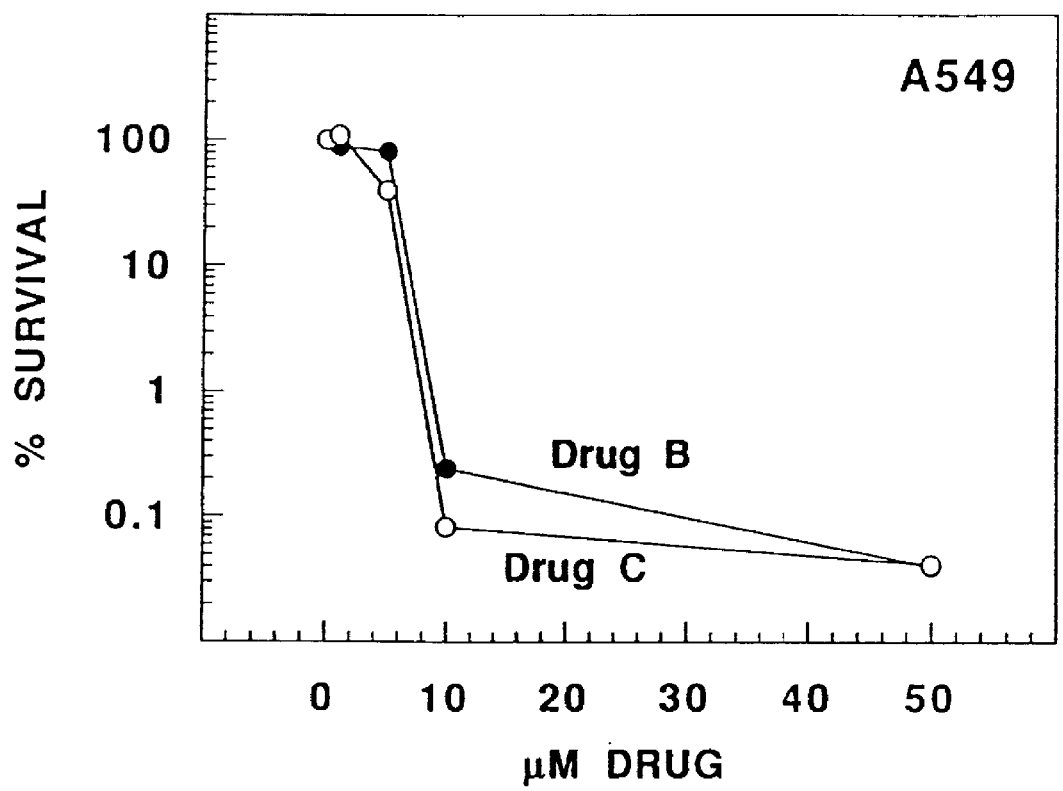
FIG. 5 is a semi-log graph depicting the fraction of cell survival of A549 lung cancer cells in the presence of Drug C (dunnione, i.e., 2,3,3-trimethyl-2,3,4,5-dihydro-naphtho (2,3-b)dihydrofuran-6,7-dione) and Drug B (2,3-dimethyl-2,3,4,5-dihydro-naphtho (2,3-b)dihydrofuran-6,7-dione, also called 3-NOR-dunnione).
Figure 6:
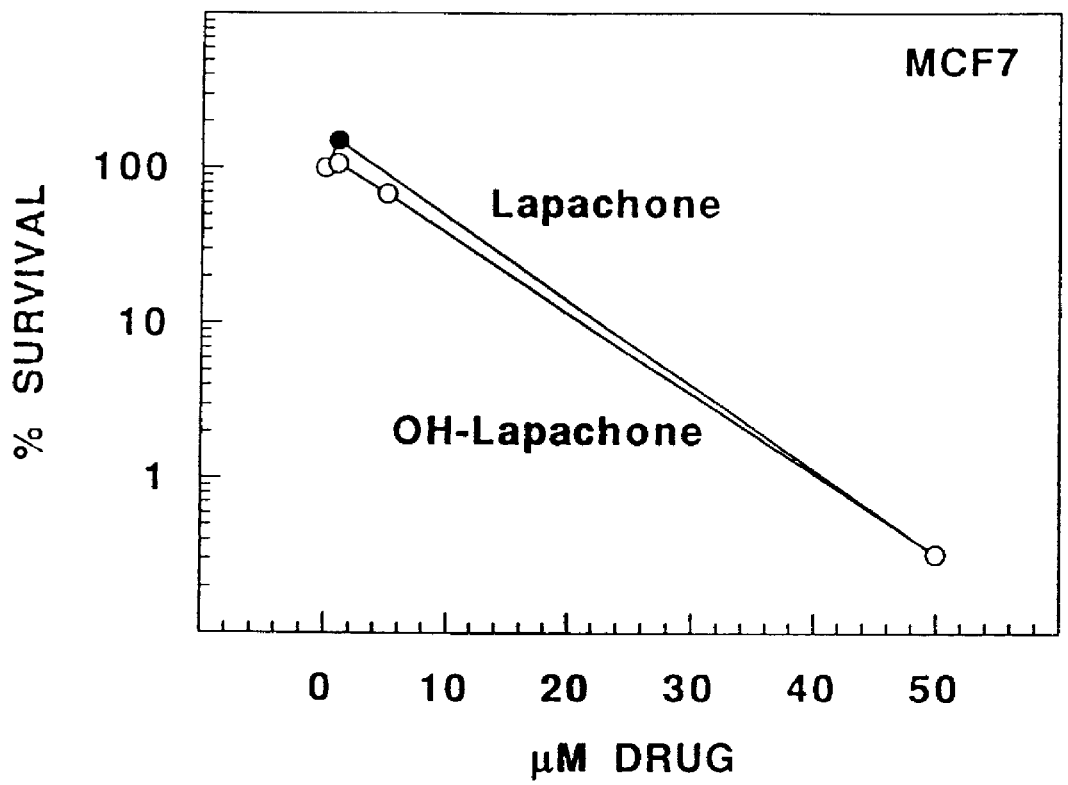
FIG. 6 is a semi-log graph depicting the fraction of cell survival of breast cancer cells MCF7 in the presence of β-lapachone and 3-hydroxy-β-lapachone.
Figure 7:
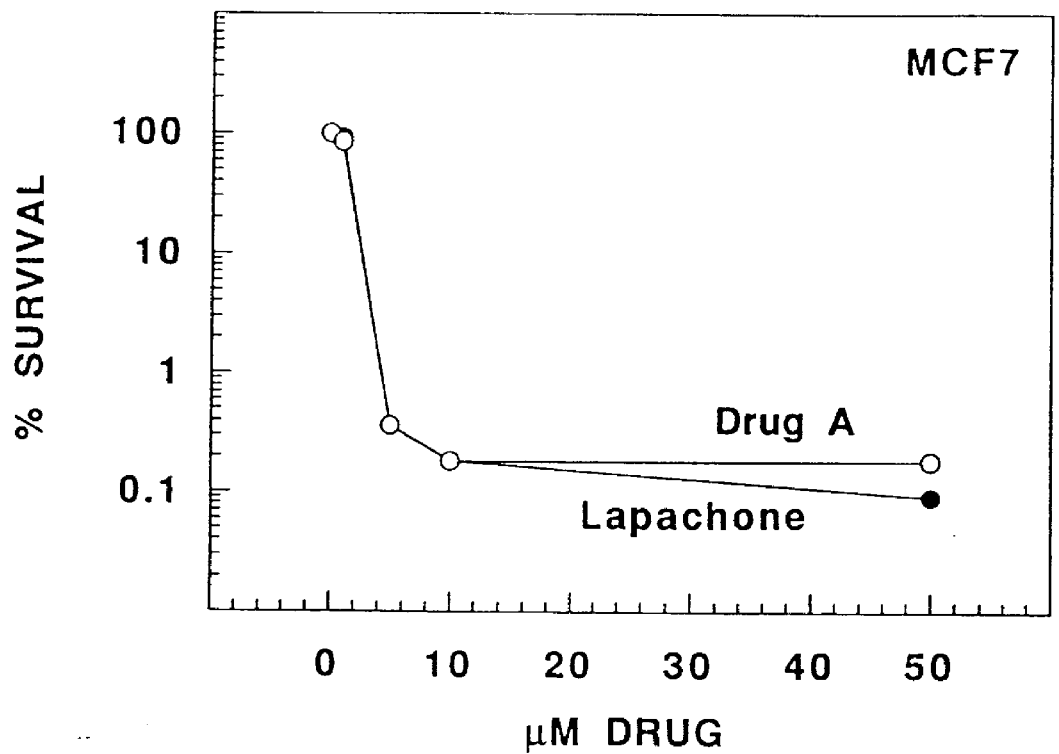
FIG. 7 is a semi-log graph depicting the fraction of cell survival of breast cancer cells MCF7 in the presence of β-lapachone and Drug A (2-methyl-2,3,4,5-tetrahydro-naphtho (2,3-b)dihydrofuran-6,7-dione, also called 3,3-DINOR-dunnione).
Figure 8:
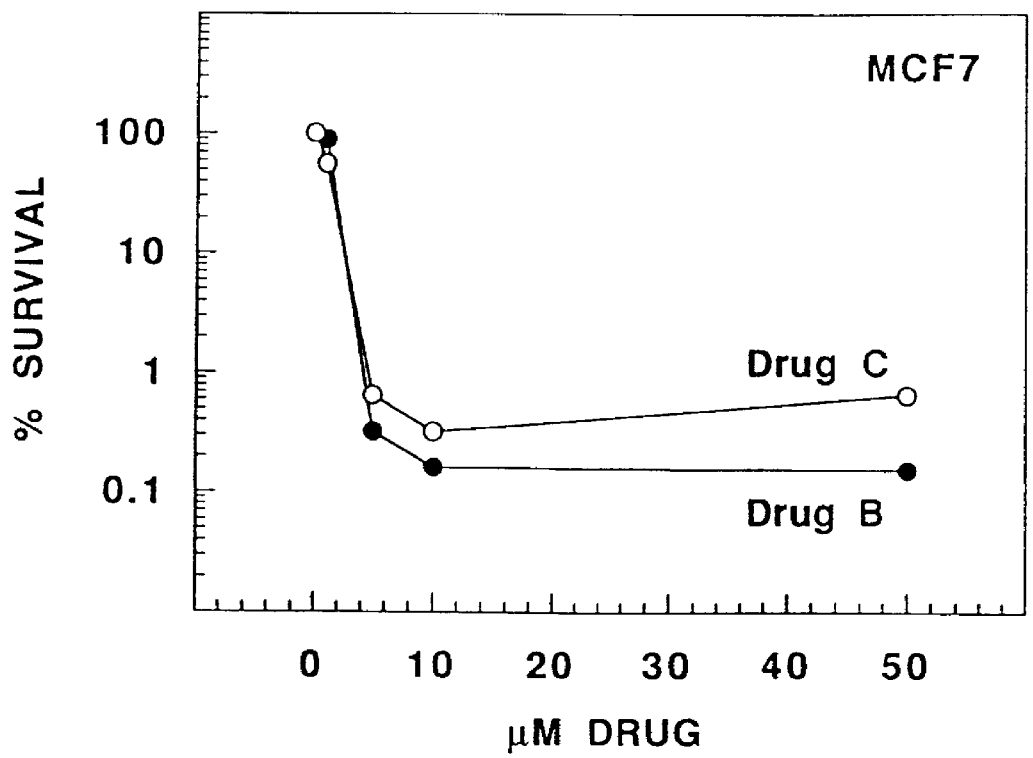
FIG. 8 is a semi-log graph depicting the fraction of cell survival of breast cancer cells MCF7 in the presence of Drug C (dunnione) and Drug B (2,3-dimethyl-2,3,4,5-dihydro-naphtho(2,3-b)dihydrofuran-6,7-dione, also called 3-NOR-dunnione).

The $ED_{50}$ results of the testing, and the respective figures which graphically illustrate the test results are summarized as follows:

| Cell Line | Colony Experiments $ED_{50}$ Values | |
|---|---|---|
| HT29 | $ED_{50}$ (Lap) = 4.8 μM | FIG. 1 |
|  | $ED_{50}$ (OH-Lap) = 15.4 μM |  |
| BE | $ED_{50}$ (Lap) = 8 μM | FIG. 2 |
|  | $ED_{50}$ (OH-Lap) = 0.6 μM |  |
| A549 | $ED_{50}$ (Lap) = 6.1 μM | FIG. 3 |
|  | $ED_{50}$ (OH-Lap) = 18 μM |  |
| A549 | $ED_{50}$ (Lap) = 5.8 μM | FIG. 4 |
|  | $ED_{50}$ (Drug A) = 6 μM |  |
| A549 | $ED_{50}$ (Drug B) = 5.6 μM | FIG. 5 |
|  | $ED_{50}$ (Drug C) = 4.3 μM |  |
| MCF7 | $ED_{50}$ (Lap) = 9.8 μM | FIG. 6 |
|  | $ED_{50}$ (OH-Lap) = 7.7 μM |  |
| MCF7 | $ED_{50}$ (Lap) = 1.6 μM | FIG. 7 |
|  | $ED_{50}$ (Drug A) = 1.6 μM |  |
| MCF7 | $ED_{50}$ (Drug B) = 1.4 μM | FIG. 8 |
|  | $ED_{50}$ (Drug C) = 1.4 μM |  |

Effectiveness against colon cancer:

The cell lines HT29 and BE are both human colon cancer cell lines which are used to test the effectiveness of a given agent against cancer cell growth and proliferation. FIGS. 1 and 2 depict the cell survival in cultures of HT29 and BE upon the addition of β-lapachone (●) and 3-hydroxy-β-lapachone (○). The HT29 and BE cell cultures were prepared and tested according to the protocol given above.

As clearly shown in FIGS. 1 and 2, at a concentration of approximately 10 μM, β-lapachone already significantly impacts upon the ability of the HT29 and BE cells to reproduce. 3-Hydroxy-β-lapachone also significantly limits the reproductive ability of these cancer cell lines.

In FIG. 1, the $ED_{50}$ value for β-lapachone is 4.8 μM, and the $ED_{50}$ for 3-hydroxy-β-lapachone is 15.4 μM. (Bear in mind that the Y-axes in FIGS. 1–8 are logarithmic, not linear.)

For the BE cell line tested, the $ED_{50}$ for the β-lapachone plot shown in FIG. 2 is 8 μM, while the $ED_{50}$ for 3-hydroxy-β-lapachone is 0.6 μM.

The numerical values and standard deviations of the individual data points presented in FIGS. 1 and 2 are tabulated in Tables 1 and 2, respectively.

TABLE 1

Fraction of Cell Survival
HT29 With β-Lapachone and 3-Hydroxy-β-lapachone (FIG. 1)

| Concentration of Drug (μM) | Fraction of Cell Survival | Standard Deviation |
|---|---|---|
| 0 | 0.9868 | 0.0935 |
| 1 | 0.9669 | 0.1228 |
| 5 | 0.4901 | 0.0480 |
| 10 | 0.0000 | 0.0000 |
| 50 | 0.0000 | 0.0000 |
| 0 | 1.0132 | 0.0688 |
| 2 | 1.5232 | 0.1125 |
| 10 | 1.1854 | 0.0532 |
| 20 | 0.0232 | 0.0020 |
| 100 | 0.0000 | 0.0000 |

TABLE 2

Fraction of Cell Survival
BE With β-Lapachone and 3-Hydroxy-β-lapachone (FIG. 2)

| Concentration of Drug (μM) | Fraction of Cell Survival | Standard Deviation |
|---|---|---|
| 0 | 1.1111 | 0.0731 |
| 2 | 0.0117 | 0.0082 |
| 10 | 0.1579 | 0.0126 |
| 20 | 0.0439 | 0.0102 |
| 100 | 0.0000 | 0.0000 |
| 0 | 0.8889 | 0.0850 |
| 2 | 0.9293 | 0.1280 |
| 10 | 0.3918 | 0.0627 |
| 20 | 0.0102 | 0.0046 |
| 100 | 0.0000 | 0.0000 |

Effectiveness against lung cancer:

FIGS. 3, 4, and 5 depict the results of studies of the effectiveness of several different tricyclic o-naphthoquinones against lung cancer cells A549. The compounds tested were β-lapachone, 3-hydroxy-β-lapachone, 3,3-DINOR-dunnione (designated "Drug A" in the figures), 3-NOR-dunnione (designated "Drug B" in the figures) and dunnione itself (designated "Drug C" in the figures). A legend for the figures is provided below. The cell lines were cultured and the compounds evaluated according to the standard protocol described above.

FIGURE LEGEND

| Designation | Formula | Trivial Name |
|---|---|---|
| Drug A |  | 3,3-DINOR-dunnione |
| Drug B |  | 3-NOR-dunnione |
| Drug C |  | dunnione |
| Drug D |  | 3,3-DINOR-2,3-dehydrodunnione |

All of the compounds tested exhibited excellent $ED_{50}$ values against the proliferation of A549 lung cancer cells.

For instance, in FIG. 3, the $ED_{50}$ for β-lapachone (●) is 6.1 μM, and the $ED_{50}$ for 3-hydroxy-β-lapachone (○) is 18 μM. The data in FIG. 4 indicate that $ED_{50}$ (β-lapachone) (●)=5.8 μM, and $ED_{50}$ (3,3-DINOR-dunnione) (○)=6 μM. $ED_{50}$ (3-NOR-dunnione) (●)=5.6 μM in FIG. 5, and the $ED_{50}$ for dunnione (○) itself is a remarkably low 4.3 μM.

The numerical values and standard deviations of the individual data points presented in FIGS. 3, 4, and 5 are tabulated in Tables 3–8, below:

TABLE 3

Fraction of Cell Survival
A549 With β-Lapachone (FIG. 3)

| Concentration of Drug (μM) | Fraction of Cell Survival | Standard Deviation |
|---|---|---|
| 0 | 1.5556 | 0.0327 |
| 1 | 2.6528 | 0.0667 |
| 5 | 1.5833 | 0.0899 |
| 10 | 0.0000 | 0.0000 |
| 50 | 0.1771 | 0.1017 |

TABLE 4

Fraction of Cell Survival
A549 With 3-Hydroxy-β-lapachone (FIG. 3)

| Concentration of Drug (μM) | Fraction of Cell Survival | Standard Deviation |
|---|---|---|
| 0 | 0.4444 | 0.0197 |
| 1 | 3.0417 | 0.0978 |
| 5 | 2.3924 | 0.0637 |
| 10 | 1.5330 | 0.0431 |
| 50 | 0.0000 | 0.0000 |

TABLE 5

Fraction of Cell Survival
A549 With β-Lapachone (FIG. 4)

| Concentration of Drug (μM) | Fraction of Cell Survival | Standard Deviation |
|---|---|---|
| 0 | 1.0161 | 0.0818 |
| 1 | 0.8552 | 0.0580 |
| 5 | 0.8966 | 0.0303 |
| 10 | 0.0069 | 0.0027 |
| 50 | 0.0000 | 0.0000 |

TABLE 6

Fraction of Cell Survival
A549 With "Drug A" (3,3-DINOR-Dunnione) (FIG. 4)

| Concentration of Drug (μM) | Fraction of Cell Survival | Standard Deviation |
|---|---|---|
| 0 | 0.9840 | 0.0585 |
| 1 | 1.1080 | 0.0705 |
| 5 | 1.2115 | 0.0238 |
| 10 | 0.0172 | 0.0044 |
| 50 | 0.0023 | 0.0006 |

TABLE 7

Fraction of Cell Survival
A549 With "Drug B" (3-NOR-Dunnione) (FIG. 5)

| Concentration of Drug (μM) | Fraction of Cell Survival | Standard Deviation |
|---|---|---|
| 0 | 1.0962 | 0.0724 |
| 1 | 0.8972 | 0.1169 |
| 5 | 0.8190 | 0.0950 |
| 10 | 0.0024 | 0.0031 |
| 50 | 0.0000 | 0.0000 |

TABLE 8

Fraction of Cell Survival
A549 With "Drug C" (Dunnione) (FIG. 5)

| Concentration of Drug (μM) | Fraction of Cell Survival | Standard Deviation |
|---|---|---|
| 0 | 0.9088 | 0.1003 |
| 1 | 1.0962 | 0.0888 |
| 5 | 0.3997 | 0.0284 |
| 10 | 0.0000 | 0.0000 |
| 50 | 0.0000 | 0.0000 |

Effectiveness against breast cancer:

In the same fashion as the above tests, several lapachone and dunnione derivatives were evaluated for their efficacy in inhibiting the proliferation of breast cancer cells. In this instance, the cancer cell line utilized was MCF7.

FIG. 6 depicts the fraction of cell survival for a series of MCF7 cell cultures exposed to β-lapachone (●) and 3-hydroxy-β-lapachone (○). Here, the $ED_{50}$ for β-lapachone was found to be 9.8 μM, while the $ED_{50}$ for 3-hydroxy-β-lapachone was found to be 7.7 μM.

FIG. 7 depicts a comparative cell survival study between β-lapachone (●) and 3,3-DINOR-dunnione ("Drug A") (○). In this study, the $ED_{50}$ for both β-lapachone and 3,3-DINOR-dunnione was found to be a very low 1.6 μM.

FIG. 8 depicts an identical comparative cell survival study between 3-NOR-dunnione ("Drug B") (●) and dunnione itself ("Drug C") (○). The $ED_{50}$ levels in this study were also shown to be remarkably low. For both the 3-NOR-dunnione and dunnione itself, the $ED_{50}$ was found to be 1.4 μM.

The numerical values and standard deviations of the individual data points presented in FIGS. 6, 7, and 8 are tabulated in Tables 9–14, below.

TABLE 9

Fraction of Cell Survival
MCF7 With β-Lapachone (FIG. 6)

| Concentration of Drug (μM) | Fraction of Cell Survival | Standard Deviation |
|---|---|---|
| 0 | 0.5770 | 0.0152 |
| 1 | 1.5 | 0.2665 |
| 5 | 0.0000 | 0.0000 |
| 10 | 0.0000 | 0.0000 |
| 50 | 0.0032 | 0.0010 |

TABLE 10

Fraction of Cell Survival
MCF7 With 3-Hydroxy-β-lapachone (FIG. 6)

| Concentration of Drug (μM) | Fraction of Cell Survival | Standard Deviation |
|---|---|---|
| 0 | 1.4231 | 0.0423 |
| 1 | 1.0641 | 0.0553 |
| 5 | 0.6795 | 0.0218 |
| 10 | 0.0000 | 0.0000 |
| 50 | 0.0032 | 0.0010 |

TABLE 11

Fraction of Cell Survival
MCF7 With β-Lapachone (FIG. 7)

| Concentration of Drug (μM) | Fraction of Cell Survival | Standard Deviation |
|---|---|---|
| 0 | 1.0145 | 0.0783 |
| 1 | 0.9197 | 0.0687 |
| 5 | 0.0036 | 0.0020 |
| 10 | 0.0018 | 0.0010 |
| 50 | 0.0009 | 0.0005 |

TABLE 12

Fraction of Cell Survival
MCF7 With "Drug A" (3,3-DINOR-Dunnione) (FIG. 7)

| Concentration of Drug (μM) | Fraction of Cell Survival | Standard Deviation |
|---|---|---|
| 0 | 0.9854 | 0.0579 |
| 1 | 0.8540 | 0.0389 |
| 5 | 0.0036 | 0.0020 |
| 10 | 0.0018 | 0.0010 |
| 50 | 0.0018 | 0.0005 |

TABLE 13

Fraction of Cell Survival
MCF7 With "Drug B" (3-NOR-Dunnione) (FIG. 8)

| Concentration of Drug (μM) | Fraction of Cell Survival | Standard Deviation |
|---|---|---|
| 0 | 0.8377 | 0.0593 |
| 1 | 0.0888 | 0.0444 |
| 5 | 0.0032 | 0.0020 |
| 10 | 0.0016 | 0.0010 |
| 50 | 0.0154 | 0.0035 |

TABLE 14

Fraction of Cell Survival
MCF7 With "Drug C" (Dunnione) (FIG. 8)

| Concentration of Drug (μM) | Fraction of Cell Survival | Standard Deviation |
|---|---|---|
| 0 | 1.1624 | 0.0781 |
| 1 | 0.5584 | 0.0674 |
| 5 | 0.0065 | 0.0041 |
| 10 | 0.0032 | 0.0013 |
| 50 | 0.0065 | 0.0013 |

Effectiveness against prostate cancer:

Additional biological testing was conducted to evaluate the efficacy of the tricyclic o-naphthoquinones against prostate cancer and to further evaluate the biological activity of the compounds against breast cancer. The compounds evaluated were as follows:

Drug B=3-NOR-Dunnione

Drug C=Dunnione

Drug D=3,3-DINOR-2,3-Dehydrodunnione

Table 15 lists the $IC_{50}$ determinations of Drugs B, C, and D against the human prostate cancer cell line PC-3 and the human breast cancer cell line MCF7.

TABLE 15

$IC_{50}$ Determinations of Drugs B, C, and D on Human Prostate (PC-3) and Breast (MCF7) Cell Lines

| Structures | $IC_{50}$ (μM) | |
|---|---|---|
| Naphtho(2,3-b)dihydrofurandiones | PC-3 | MCF7 |
| Drug B | 0.7 | 0.5 |
| Drug C | 0.6 | 0.7 |
| Drug D | 0.9 | 0.7 |

$IC_{50}$ calculations for each cell line were determined by DNA amount and anchorage-dependent colony formation (CF) as described elsewhere. (See Planchon et al. *Cancer Res.* 55, 3706 (1995), incorporated herein by reference.) In short, $IC_{50}$ calculations for each cell line were determined by DNA amount and anchorage-dependent colony formation (CF) assays. For the CF assay, cells were seeded at 500 viable cells/well in 6-well plates and incubated overnight, then treated with equal volumes of media containing β-lapachone at final concentrations ranging from 0.005 to 50 μM in half-log increments (controls were treated with 0.25% DMSO, equivalent to the highest dose of β-lapachone used) for 4 hours or for continuous 12 hour exposures. Plates (3 wells/condition) were stained with crystal violet, and colonies of >50 normal-appearing cells were enumerated. $IC_{50}$ values for various cells were calculated using drug doses with numbers of colonies surrounding 50% of control. For DNA assays, plates were harvested for $IC_{50}$ determinations 8 days after treatment using a CytoFluor 2350 fluorescence measurement system (Millipore). Six-well samplings were included in the calculation of DNA fluor units for each dose. A graph of β-lapachone dose versus percentage control DNA in fluor units was used to calculate each $IC_{50}$. The cells were exposed for 24 hours to the tricyclic naphthoquinones. All experiments were repeated at least twice, each in duplicate. PC-3 is an androgen-independent prostate cancer cell line.

To further study the presently described compounds, their ability to induce apoptosis (programmed cell death) in human prostate and breast cancer cell lines was evaluated. The results are encouraging in the all of the compounds tested induced apoptosis at a concentration of 5 μM.

TABLE 16

Apoptopic Effects of B, C, and D on
Human Prostate (PC-3) and Breast (MCF7) Cancer Cell Lines

| Structures Naphtho(2,3-b) dihydrofurandiones | Apoptosis Observed Concentrations | | | | | |
|---|---|---|---|---|---|---|
| | 1 μm | 5 μm | 10 μm | 25 μm | 50 μm | 100 μm |
| Drug C | − | + | + | + | + | + |
| Drug B | + | + | + | + | + | + |
| Drug D | + | + | + | + | + | + |

Quantification of apoptotic cells and alterations in cell cycle distribution were determined 24 hours after drug treatment (1.0–100 μm; 4 h) by flow cytometry and DNA laddering as described by Planchon et al. supra. Experiments were repeated at least three times, each in duplicate. The above results apply to both the PC-3 and MCF7 cell lines.

An illustrative method to determine apoptosis proceeds as follows: Cells ($1\times10^6$/condition) were treated with or without various concentrations of β-lapachone, topotecan, or camptothecin for various times. Trypsinized or pelleted cells were washed with ice-cold Tris/saline solution (10 mM Tris (pH 7.0) and 50 mM NaCl), fixed in 90% ethanol-Tris/saline, and stored at −4° C. Cells were washed with phosphate-citric acid buffer (0.2M $Na_2HPO_4$ and 0.1M citric acid (pH 7.8)) and stained with a solution containing 0.2% NP40, RNase A (7000 units/ml), and 33 μg/ml propidium iodide at 4° C. for 10 minutes. Stained nuclei were then analyzed for DNA-propidium fluorescence using a Becton Dickinson FACScan (San Jose, Calif.) at a laser setting of 36 mW and an excitation wavelength of 488 nm. Resulting DNA distributions were then analyzed for proportion cells in apoptosis, $G_0/G_1$, S, and $G_2/M$ of the cell cycle. Data was analyzed by ModFit (Verity Software House, Inc., Topsham, ME). All experiments were repeated at least three times, each in duplicate.

Cells from the above conditions were also analyzed for the formation of 180–200bp DNA laddering, which can be diagnostic for certain cells undergoing apoptosis. Treated and control cells were washed twice with PBS containing 1 mM EDTA at ambient temperature and lysed in 10 mM EDTA, to mM Tris-HC1 (pH 8.0), 0.5% (w.v) sodium lauryl sarkosinate, and 0.5 mg/ml RNase A for at least 1 hour at 37° C. and then with 1.0 mg/ml proteinase K at 37° C. for at least 1 hour. Loading buffer (10 mM EDTA, 1% (w/v) low melting point agarose, 0.25% (w.v) bromophenol blue, and 40% (w.v) sucrose) was then added (10% final concentration), and heated (70° C.) samples were loaded onto presolidified, 1.8% (w/v) agarose gels containing 0.1 /μg/ml ethidium bromide using end-cut Rainin (Woburn, Mass.) 1-ml pipette tips to avoid DNA shearing. Agarose gels were run at 65 V/cm for 10 minutes and then at 15 V/cm overnight in 1×TAE (1.0M Tris-acetate (pH 7.5) and 10 mM EDTA) running buffer.

Inhibition of Topoisomerase I and II:

Once it had been discovered that the tricyclic compounds described herein would not only inhibit cell growth, but would actively induce cell death via apoptosis, a mechanism to account for these biological effects was investigated. As shown in Table 17, it was found that the compounds of the present invention are inhibitors of Topoisomerase I (Topo I). By inhibiting the function of Topo I, which catalyzes the unwinding of DNA strands prior to replication, it is hypothesized that the compounds described above induce cell death by preventing access to the genetic information necessary to carry on normal cellular operations.

TABLE 17

Inhibition of the Catalytic Activity of
Topoisomerase I by Drugs B, C, and D

| Structures Naphto (2,3-b) furan diones | Inhibition of Topoisomerase I | | | |
|---|---|---|---|---|
| | 1 μm | 10 μm | 100 μm | 1 mM |
| Drug C | − | + | + | + |
| Drug B | + | + | + | + |
| Drug D | − | − | + | + |

Topoisomerase I (Topo I) from human placenta (3.0 units) was incubated with various concentrations of Drug B, C, or D for 10 min. at 37° C. p36B4 Supercoiled plasmid DNA (1.5 μg) was then added to initiate DNA unwinding reactions. Topo I DNA unwinding activity was measured as described in Hsiang et al. *J. Biol. Chem.*, 260, 14873 (1985), incorporated herein by reference.

Topoisomerase I enzymatic activity can be assayed in the following manner: supercoiled DNA unwinding assays using purified human placenta Topo I (TopoGEN, Inc., Columbus, Ohio) were performed with or without drug addition to assess the inhibitory effects of β-lapachone, camptothecin, and topotecan under various reaction conditions. Enzymatic assays were performed in two basic fashions. In the first reaction sequence, Topo I (3.0 units) was incubated with increasing concentrations of β-lapachone, camptothecin (or topotecan), or DMSO for 5 minutes at 37° C. in Topo I reaction buffer (without dATP). p36B4 Supercoiled DNA (1.5 μg) was then added to begin the reactions, and aliquots were taken at various times. In the second reaction sequence, p364B4 DNA (1.5 μg) was incubated with various β-lapachone, camptothecin, or topotecan concentrations for 5 minutes at 36° C., and Topo I (3.0 units) was added at t=0. Aliquots were removed at various times to follow DNA unwinding reactions and immediately treated with SDS-proteinase K at 65° C. and loaded onto 0.7% agarose gels; supercoiled (form 1) substrate was separated and quantified from reaction intermediates (R) and open circular (form II) product. On most agarose gels, DNA molecular weight markers (λDNA cut from EcoRl-Hindlll (marked "Lambda EcoRI DNA Marker"); Sigma Chemical Co., St. Louis, Mo.), linearized p36B4 plasmid DNA (cut with PstI), and p36B4 plasmid DNA substrate were concomitantly added. Gels were stained with 50 μg/ml ethidium bromide and destained for 30 minutes in distilled water; the loss of form I relative to total DNA loaded was quantified by densitometric scans of photographic negatives (type 55; Polaroid, Cambridge, Mass.). Enzyme inhibition was defined as the effects of various drugs on Topo I activity compared to control (DMSO alone) reactions.

Figure 9A:
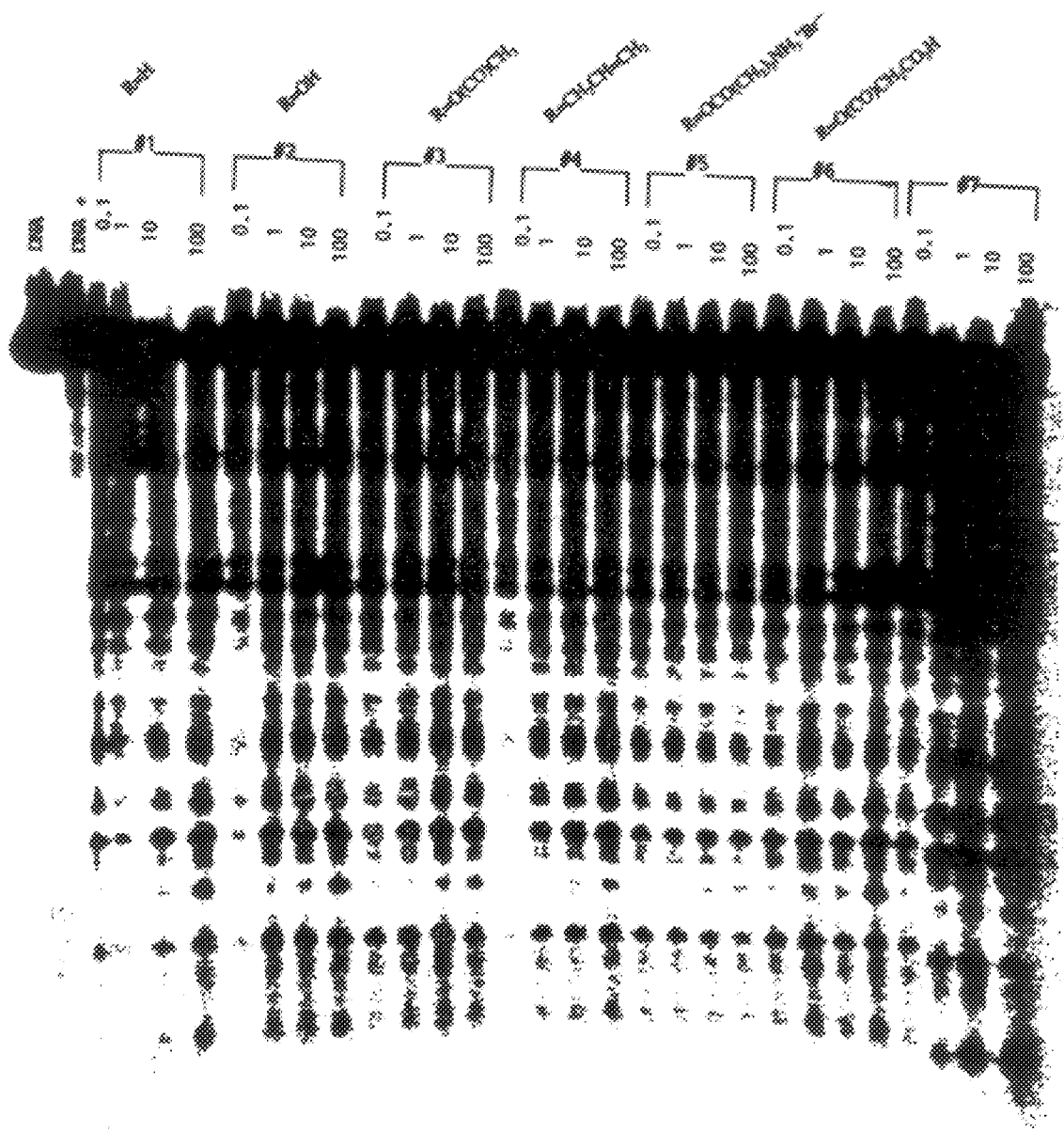
FIGS. 9A and 9B combined depict an electrophoresis plate run illustrating the ability of several of the compounds described herein to induce Topoisomerase II-mediated cleavage of DNA. The far left-hand lane of FIG. 9A is a lane containing DNA alone and the adjacent lane contains DNA and Topo II. The groups of lanes labeled 1–9 in FIGS. 9A and 9B depict varying concentrations of different compounds described herein in combination with DNA and Topo II.
Figure 9B:
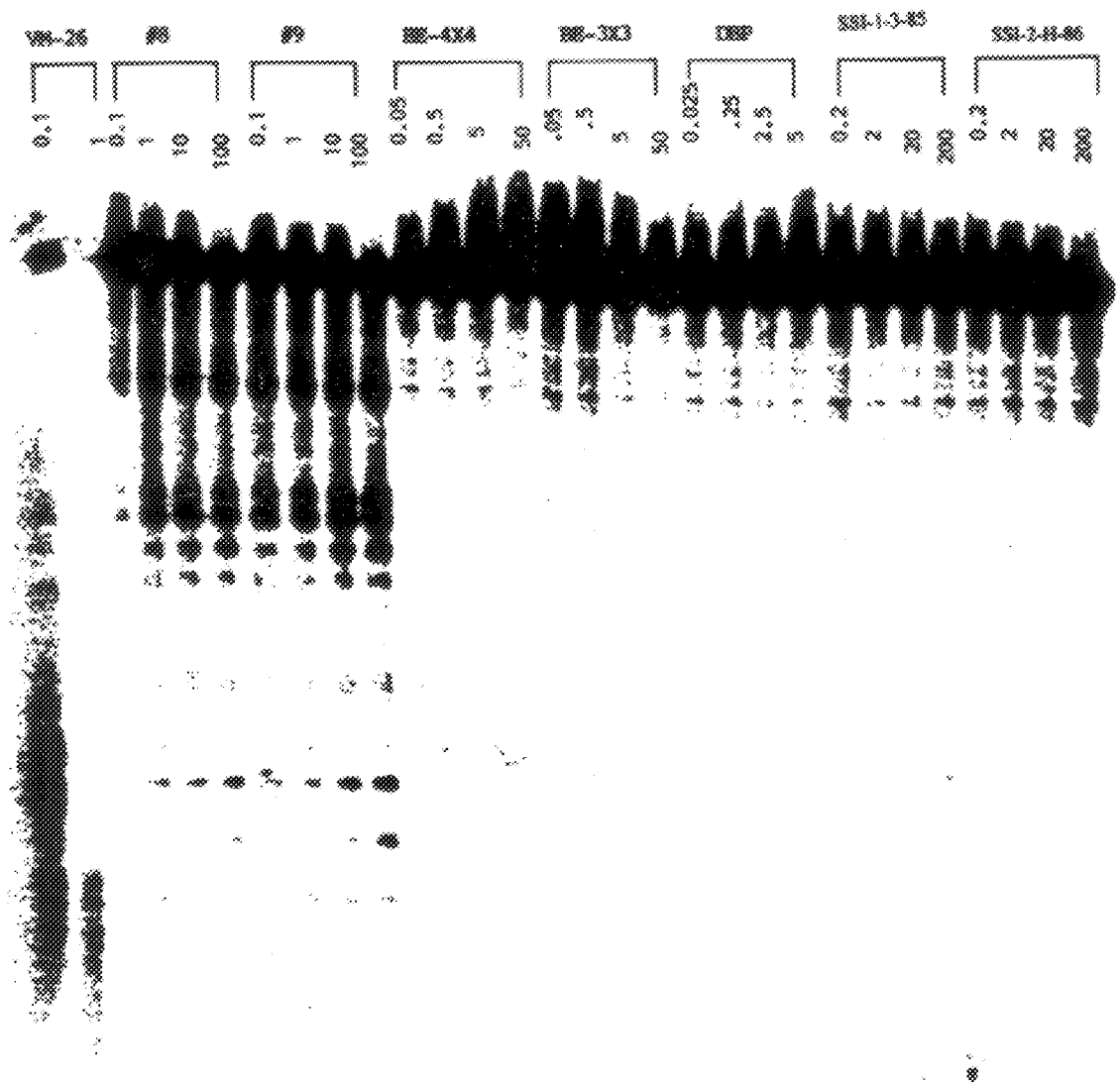

Analogous experiments to assay the ability of several of the compounds described herein to induce Topoisomerase II (Topo II)-mediated DNA cleavage were also performed. The results of one such experiment are depicted in the electrophoretegram of FIGS. 9A and 9B. Here, DNA was incubated in the presence of Topo II and several different compounds described herein. The electrophoresis plate run depicted in FIGS. 9A and 9B shows that the naphthoquinone derivatives described herein have the ability to form Topo II-drug DNA-cleaving complexes.

As detailed herein, the β-lapachone and dunnione analogs of the present invention have been shown to exhibit a broad spectrum of anti-cancer activity. The analogs are equally potent against human multidrug-resistant cancer cells. The gel depicted in FIGS. 9A and 9B show that DNA Topo II is an intracellular target of the compounds described herein. The compounds stimulate Topo II-mediated DNA cleavage. The compounds also induce Topo II-mediated cleavage using purified mammalian Topo II. However, unlike other Topo II drugs, the DNA cleavage patterns induced by the naphthoquinone compounds were similar to background Topo II-induced cleavage.

The compounds described herein also inhibited Topo II catalytic activity in a P4 knotting assay (data not shown). The inhibition appears to be a specific interaction of the compounds with the Topo II-mediated reaction: the compounds induce very slight unwinding in a plasmid DNA unwinding assay. Furthermore, the compounds tested induced DNA cleavage and protein-DNA cross-links in cultured mammalian cells. This suggests that the anti-tumor activity of the compounds is due to a specific interaction with Topo II.

A legend for the compounds which were tested in FIGS. 9A and 9B is as follows:

Legend for Figs. 9A and 9B:

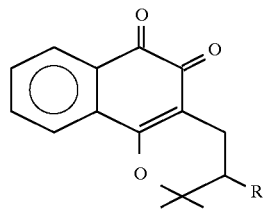

Lane 1: R=H (β-lapachone)
Lane 2: R=OH
Lane 3: R=OC(O)CH$_3$
Lane 4: R=CH$_2$CH=CH$_2$
Lane 5: R=OC(O)CH$_2$CH$_2$NH$_3$$^+$Br
Lane 6: R=OC(O)CH$_2$CO$_2$H
Lane 7: 4-pentyloxy-1,2-naphthoquinone

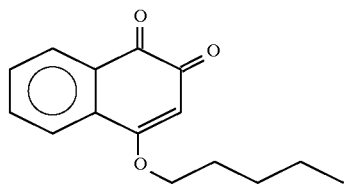

Lane 8: "Drug B," 3-NOR-dunnione
Lane 9: dunnione

Lane 7 contains a 4-alkoxy-1,2-naphthoquinone, namely 4-pentyloxy-1,2-naphthoquinone. 4-(C$_1$–C$_6$ alkoxy)-1,2-naphthoquinones, as well as several other types of 4-substituted-1,2-naphthoquinones, including 4-(C$_1$–C$_6$ alkenyloxy)-1,2-naphthoquinones, 4-(C$_1$–C$_6$ carbonyloxy)-1,2-naphthoquinones, 4-(C$_1$–C$_6$ aryloxy)-1,2-naphthoquinones, 4-(C$_1$–C$_6$ heteroaryloxy)-1,2-naphthoquinones, 4-(benzyloxy)-1,2-naphthoquinone, 4-(C$_3$–C$_6$ cycloaryloxy)-1,2-naphthoquinones, and 4-(C$_3$–C$_6$ heterocycloaryloxy)-1,2-naphthoquinones can be synthesized by reacting a silver salt of lawsone with a haloalkane in a suitable solvent (e.g., benzene). The resulting solution is then washed with ethyl acetate to dissolve the organic products and then filtered to remove the silver salts. The ethyl acetate solution is washed with NH$_4$OH, followed by NaHSO$_3$. The NaHSO$_3$ extracts are combined, treated with Na$_2$CO$_3$ and extracted with CH$_2$Cl$_2$. The CH$_2$Cl$_2$ extracts are combined and dried. Removal of the solvent, as by evaporation, yields the 4-alkoxy- 1,2-naphthoquinone product. If desired, the product can be further purified by re-crystallization from benzene-ligroin.

The gels shown in FIGS. 9A and 9B show that Topo II is an intracellular target of β-lapachone, dunnione, and their derivatives. In the far left-hand lane of FIG. 8A, DNA alone is shown. Moving to the right, the next lane contains DNA and Topo II (mammalian). Lanes 1–9 of FIGS. 9A and 9B contain a series of concentrations of drugs (see Legend, above) in the presence of DNA and Topo II. Each set of lanes for each drug spans 3 orders of magnitude in concentration (0.1, 1, 10, and 100 μM). In FIG. 9A, the second lane from the left, which contains DNA and Topo II, shows very little DNA cleavage. The far left-hand lane of FIG. 9A, which contains DNA alone, shows no cleavage products. However, Lanes 1–9, which contain DNA, Topo II, and a drug according to the present invention, show extensive DNA cleavage. The wide range of differently-sized cleavage products indicates that the cleavage is extensive and heterogeneous.

Pharmaceutical Dosage Forms

The above-described compounds being effective to inhibit the growth of cancer cells, the compounds are suitable for the therapeutic treatment of neoplastic conditions in mammals, including humans. Cancer cell growth inhibition at pharmacologically-acceptable concentrations has been shown in human breast cancer, colon cancer, lung cancer, and prostate cancer cell lines, as described above.

The compounds described herein are administratable in the form of tablets, pills, powder mixtures, capsules, injectables, solutions, suppositories, emulsions, dispersions, food premixes, and in other suitable forms. The pharmaceutical dosage form which contains the compounds described herein is conveniently admixed with a non-toxic pharmaceutical organic carrier or a non-toxic pharmaceutical inorganic carrier. Typical pharmaceutically-acceptable carriers include, for example, mannitol, urea, dextrans, lactose, potato and maize starches, magnesium stearate, talc, vegetable oils, polyalkylene glycols, ethyl cellulose, poly (vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical dosage form may also contain non-toxic auxiliary substances such as emulsifying, preserving, or wetting agents, and the like.

EXAMPLES

The following Examples are provided solely to aid in a clear understanding of the presently claimed invention. The following Examples do not limit the scope of the invention described above or claimed herein in any fashion.

Preparation of C-allyl and O-allyl ether derivatives of lawsone

With reference to Reaction I, above, lawsone (2-hydroxy-1,4-naphthoquinone) (52.25 g, 300 mmol) was dissolved in anhydrous DMSO (350 mL) at 23° C. The solution was cooled to −78° C., and lithium hydride (2.50 g, 315 mmol) was added to the solid. The solid solution was then allowed to warm up slowly to 23° C. When gas evolution subsided, lithium iodide (10.0 g, 75 mmol) was added, followed by the allyl bromide (34.6 mL, 300 mmol), which was added dropwise. The mixture was stirred for 5 hours at 45° C. and then for 10 hours at 23° C. After quenching the reaction with ice (200 g), water was added to the reaction (700 mL), followed by concentrated HCl (70 mL) and ethyl acetate (500 mL). Undissolved solids were collected by filtration and were confirmed to be the allyloxy-1,4-naphthoquinone (14, 20 g, 30%).

Dimethylallyloxy-1,4-naphthoquinone (14, R=R'=Me): $^1$H NMR (CDCl$_3$. 300 MHz): δ 8.20–8.00 (m, 2H), 7.86–7.58 (m, 2H), 6.16 (s, 1H), 4.49 (t, J=6.8 Hz. 1H), 4.59 (d, J=6.8 Hz, 2H), 1.81 (s, 3H), 1.76 (s, 3H).

2-Methylallyloxy-1,4-naphthoquinone (14, R=H, R'=Me): mp 136.0–137.0° C., $^1$H NMR (CDCl$_3$, 300 MHz) δ 8.13 (dd, J=7, 2 Hz, 1H), 8.08 (dd, J=7, 2 Hz, 1H), 7.75 (dt, J=7, 2 Hz, 1H), 7.70 (dd, J=7, 2 Hz, 1H), 6.17 (s, 1H), 6.00–5.90 (m, 1H), 5.8–5.7 (M, 1H), 4.53 (d, J=6 Hz, 2H), 1.78 (d, J=6 Hz, 3H).

2-Allyloxy-1,4-naphthoquinone (14, R=R'=H): $^1$H NMR (CDCl$_3$, 300 MHz) δ 8.22–8.04 (m, 2H), 7.94–7.66 (m, 2H), 6.17 (s, 1H), 6.15–5.95 (m, 1H), 5.49(dd, J=11.6, 1.2 Hz, 1H), 5.41 (dd, J=10.5, 1.2 Hz, 1H), 4.62 (d, J=5.6 Hz, 2H).

The ethyl acetate layer was then separated and aqueous layer extracted again with more ethyl acetate (250 mL). The combined organic layers were then extracted with 5% aqueous NaHCO$_3$. The NaHCO$_3$ extracts were acidified with concentrated HCl and the precipitate filtered. The precipitate was shown to be unreacted lawsone (10) (16.02 g, 30%).

The ethyl acetate solution was evaporated in vacuo and the residue dissolved in diethyl ether (500 mL). The ether solution was extracted with 2N NaOH (3×200 mL). The alkaline extracts were acidified with concentrated HCl and allowed to stand at 4° C. for 15 hours. The precipitate was filtered, dried, and re-crystallized from a mixture of EtOH/H$_2$O to afford (13) as yellow crystals.

3-(Dimethylallyl)-2-hydroxy-1,4-naphthoquinone (13, R=R'=Me) (28.76 g, 40%): $^1$H NMR (CDCl$_3$, 300 MHz) δ 8.12 (d, J=7.5 Hz, 1H), 8.07 (d, J=7.5, 1H), 7.75 (t, J=7.5 Hz, 1H), 7.67 (t, J=7.5 Hz, 1H), 7.29 (s, OH), 5.21 (t, J=7.3 Hz, 1H), 3.31 (d, J=7.3 Hz, 1H), 1.79 (s, 3H), 1.68 (s, 3H).

3-(Methylallyl)-2-hydroxy-1,4-naphthoquinone (13, R=H, R'=Me) (36%): mp 130.5–131.5° C.; $^1$H NMR (CDCl$_3$, 300 MHz) δ 8.13 (dd, J=7.5, 1.3 Hz, 1H), 8.08 (dd, J=7.5, 1.3 Hz, 1H), 7.76 (td, J=7.5, 1.3 Hz, 1H), 7.68 (td, J=7.5, 1.3 Hz, 1H), 7.36 (s, OH), 5.40–5.70 (m, 2H), 3.29 (d, J=6.0 Hz, 2H), 1.62 (d, J=6.0 Hz, 2H).

3-Allyl-2-hydroxy-1,4-naphthoquinone (13, R=R'=H) (39%): $^1$H NMR (CDCl$_3$, 300 MHz) δ 8.13 (dd, J=7.7, 1.1 Hz, 1H), 8.09 (dd, J=7.6, 1.1 Hz, 1H), 7.76 (dt, J=7.5, 1.5 Hz, 1H), 7.69 (dt, J=7.5, 1.4 Hz, 1H), 7.33 (s, OH), 6.08–5.80 (M, 1H), 5.17 (dd, J=17.1, 1.6 Hz, 1H), 5.05 (dd, J=10.0, 1.5 Hz, 1H), 3.37 (dt, J=6.5, 1.4 Hz, 2H).

The Claisen rearrangement

Referring now to Reaction III, above, a solution of (14) (20 g) in toluene (250 mL) was heated to reflux. The solids dissolved gradually as the temperature increased and a clear red-pink solution resulted. After heating under reflux for 1.5 h, the solution was allowed to cool and 2N NaOH (100 mL) was added. The solution was filtered to separate unreacted ally ether (14) (2.24 g, 11%). The aqueous layer was separated and the toluene layer was extracted with more 2N NaOH (2×50 mL). The combined aqueous layers were acidified with concentrated HCl and extracted with ethyl acetate. The organic extracts were dried, concentrated in vacuo, and the residue re-crystallized from EtOH/H$_2$O to afford (17).

3-(Dimethylallyl)-2-hydroxy-1,4-naphthoquinone (17, R=R'=Me) (12.67 g, 63%): $^1$H NMR (CDCl$_3$, 300 MHz) δ 8.10–8.00 (m, 2H), 7.84 (s, OH), 7.80–7.60 (m, 2H), 6.29 (dd, J=17.5, 10.6 Hz, 1H), 5.04–4.93 (m, 2H), 1.57 (s, 6H).

3-(Methylallyl)-2-hydroxy-1,4-naphthoquinone (17, R=H, R'=Me) (30%): $^1$H NMR (CDCl$_3$, 300 MHz) δ 8.12 (dd, J=7.7, 1.1 Hz, 1H), 8.07 (dd, J=7.6, 1.2 Hz, 1H), 7.76 (dt, J=7.5, 0.9 Hz, 1H), 7.68 (dt, J=7.5, 1.3 Hz, 1H), 6.20 (ddd, J=17.3, 10.1. 7.4 Hz, 1H), 5.14 (dd, J=17.1, 1.5 Hz, 1H), 5.02 (dd, J=10.1, 1.3 Hz, 1H), 3.99 (m, 1H), 1.41 (d, J=7.1 Hz, 3H).

Preparation of β-lapachone and analogs
Cyclization via treatment with strong acid One technique to form the third ring of the tricyclic compounds is to treat the allyl intermediate with concentrated acid. With reference to Reactions II and III, concentrated sulfuric acid (70 mL) was added to lapachol (13) (11.26 g) (or 17 in Reaction III) at 23° C. After stirring until all solids dissolved (approximately 15 minutes), the mixture was poured into water (200 mL) and filtered to afford β-lapachone (15, R5=R6=Me) (11.11 g, 99%).

Re-crystallization from diethyl ether gave β-lapachone as orange needles (10.45 g, 94% recovery): mp 154–155.5° C., $^1$H NMR (CDCl$_3$, 300 MHz) δ 8.06 (d, J=7.7 Hz, 1H), 7.81 (d, J=7.7 Hz, 1H), 7.64 (t, J=7.7 Hz, 1H), 7.50 (t, J=7.5 Hz 1H), 2.58 (t, J=6.7 Hz, 2H), 1.86 (t, J=6.7 Hz, 2H), 1.47 (s, 6H).

Monomethyl-β-lapachone (15, R=H, R'=Me) (48% along with 22% α-isomer after silica gel chromatography): mp 164–165° C.; $^1$H NMR (CDCl$_3$, 300 MHz) δ 8.07 (dd, J=7.6, 1.5 Hz. 1H), 7.82 (dd, J=7.6, 1.2 Hz, 1H), 7.65 (dd, J=7.6, 1.5 Hz, 1H), 7.51 (dd, J=7.6, 1.2 Hz, 1H), 4.40 (dqd, J=10, 6.3, 3 Hz, 1H), 2,71 (ddd, J=17.5, 5.5, 3.5 Hz, 1H), 2.46 (ddd, J=17.5, 10.7, 6.0 Hz, 1H), 2.11 (dddd, J=14, 6, 3.5, 3, 1H), 1.71 (dddd, J=14, 10.7, 10, 5.5 Hz, 1H), 1.54 (d, J=6.3 HZ, 3H).

Dunnione (16, R=R'=Me): $^1$H NMR (CDCl$_3$, 300 MHz) δ 8.04 (d, J=7.5 Hz, 1H), 7.68–7.50 (m, 3H), 4.67 (q, J=6.7 Hz, 1H), 1.47 (d, J=6.7 Hz, 3H), 1.45 (s, 3H), 1.27 (s, 3H).

3-NOR-dunnione (16, R=H, R'=Me, R2 and R4=H) (30%): $^1$H NMR (CDCl$_3$, 300 MHz) δ 8.08 (d, J=7.4 Hz, 1H), 7.72–7.50 (m, 3H), 5.24–5.12 (m, 1H), 3.60–3.48 (m, 1H), 1.54 (d, J=6.7 Hz, 3H), 1.24 (d, J=7.1 Hz, 3H).

Cyclization via epoxidation to yield 3-substituted lapachones:

Referring now to Reaction IV, 3-hydroxy-β-lapachone (19) and derivatives thereof can be synthesized by forming an epoxide intermediate followed by ring closure. An illustrative synthesis of 3-hydroxy-β-lapachone (19, R5=R6=Me, R7=OH) proceeds as follows:

Lapachol (12.11 g, 50 mmol) was dissolved in CH$_2$Cl$_2$ (250 mL) at 23° C. The solution was cooled to 0° C., which caused some lapachol to precipitate. To this cooled solution was added m-chloroperoxybenzoic acid (m-CPBA) (10.15 g, 85% purity, 50 mmol). The solution then was stirred for 4 hours at 23° C., and the solution filtered. The filtrate was washed with aqueous NaHCO$_3$ and dried.

The epoxide so formed (18) remains in solution. To this solution was added BF$_3$.OEt$_2$ (6.15 mL, 50 mmol) at 0° C. After stirring at 23° C. for 10 hours, the solution was washed consecutively with aqueous Na$_2$CO$_3$, 5% citric acid, and water. The organic layer was extracted with 5% NaHSO$_3$ (300 mL, 200 mL, 200 mL). The extracts were pooled. Saturated Na$_2$CO$_3$ (600 mL) was added to the pooled extracts to yield reddish precipitates. The solution containing the precipitates was cooled at 0° C. for 2 hours and filtered.

The filtrate is 3-hydroxy-β-lapachone (19, R=R'=Me, R"=H) (6.72 g, 52% for the two steps from lapachol): mp 202.5–203.5° C., ¹H NMR (CDCl₃, 300 MHz) δ 8.06 (d, J=7.6 Hz, 1H), 7.84 (d, J=7.6 Hz, 1H), 7.66 (t, J=7.6 Hz, 1H), 7.52 (t, J =7.6 Hz, 1H), 3.92 (m, 1H), 2.83 (dd, J=17.7, 4.8 Hz, 1H), 2.62 (dd, J=17.7, 5.4 Hz, 1H), 1.52 (s, 3H), 1.46 (s, 3H).

2-Hydroxy-3-(2',3'-oxo-3'methylbutyl)naphthoquinone (18). This compound can be obtained by repeating the reaction described immediately above, and isolating the epoxide by silica gel chromatography (25–100% ethyl acetate in hexanes). ¹H NMR (DMSO-d6, 300 MHz) δ 8.04–7.95 (m, 2H), 7.87–7.72 (m, 2H), 3.52 (t, J=6.5 Hz, 1H), 2.65 (d, J=6.8 Hz, 2H), 1.10 (s, 6H); ¹³C NMR (CDCl₃, 75 MHz) δ180.92 (s), 175.13 (s), 169.94 (s), 134.53 (d)<131.88 (d), 130.43 (s), 129.23 (d), 127.21 (s), 124.50 (d), 115.94 (s), 93.59 (d), 71.52 (s), 27.26 (t), 25.62 (q), 24.56 (q).

Fully-Aromatic Dunnione Analogs

With reference to Reaction V, above, the fully-aromatic derivative of dunnione, namely 2-methyl-4H,5H-naphtho(2, 3-b)furan-6,7-dione (21), can be synthesized by reacting lawsone with an aldehyde.

Illustratively, 2-hydroxy-3-propenyl-1,4-naphthoquinone (20) was synthesized, followed by ring closure to yield the fully-aromatic dunnione derivative, as follows:

Propionaldehyde (RCHO, R=propyl, 5.0 mL, 69.3 mmol) was added to a solution of concentrated HCl (2 mL) and lawsone (2.00 g, 11.5 mmol) in acetic acid (35 mL) at 60° C. After stirring for 1.25 hours, another portion of propionaldehyde was added (5.0 mL, 69.3 mmol). The solution was then stirred for an additional 1 hour. The solution was allowed to cool to room temperature, and then ice water (200 mL) was added to quench the reaction. The solution was extracted with diethyl ether (3×200 mL) and the organic fractions pooled. The combined organic layers were re-extracted with 5% $Na_2CO_3$ (8×150 mL). The aqueous extracts were also pooled and acidified with concentrated HCl. A precipitate formed which was collected by filtration to afford (20) as an orange solid. 2-Hydroxy-3-propenyl-1, 4-naphthoquinone (20) (983 mg, 40%): mp 133–134° C.; ¹H NMR (CDCl₃, 300 MHZ) δ 8.13 (d, J=7.7 Hz, 1H), 8.06 (d, J =7.5 Hz, 1H), 7.80–7.62 (m, 3H), 7.15–6.95 (m, 1H), 6.63 (d, J=16.1 Hz, 1H), 1.99 (d, J=6.8 Hz, 3H).

Ring closure to yield 2-methyl-4H, 5H-naphtho[2,3-b] furan-6,7-dione (21) can be accomplished as follows. A solution of the naphthoquinone (20) (2.26 g) and Hg(OAc)₂ (5.0 g) in acetic acid (200mL) was stirred for 10 hours at 23° C. The precipitate formed which was removed by filtration. The filtrate was poured into water (400 mL), and the resultant solution was extracted with ethyl acetate (3×200 mL). The combined extracts were washed with water (3×200 mL). After drying over $MgSO_4$, the organic layer was concentrated in vacuo, and the residue was purified by chromatography (10–20% ethyl acetate in hexane) on silica gel to give (21) as a brown-red solid.

2-Methyl-4H, 5H-naphtho(2,3-b)furan-6,7-dione (21, (3,3-DINOR-2,3-dehydrodunnione)): (549 mg, 25%) mp 158.5–160°; ¹H NMR (CDCl₃, 300 MHz) δ 8.05 (d, J=7.6 Hz, 1H), 7.68–7.57 (m, 2H), 7.43 (dt, J=7.3, 1.8 Hz, 1H), 6.45 (s, 1H) 2.43 (s, 3H); ¹³C NMR (CDCl₃, 75 MHz) δ 180.73 (s), 174.40 (s), 159.64 (s), 155.97 (s), 135.39 (d), 130.47 (d), 129.82 (d), 128.72 (s), 128.60 (s), 122.70 (s), 121.99 (d), 104.55 (d), 13.63 (q); MS m/z 69, 128, 183, 212; HRMS m/z calculated for $C_{13}H_8O_3$ (M+) 212.0473, found 212.0471.

Derivatization of 3-hydroxy-β-lapachone

Once 3-hydroxy-β-lapachone has been isolated, its hydroxyl functionality can be utilized to synthesize a wide range of 3-oxy-substituted β-lapachone derivatives. What follows are examples of a mono-acid derivative, an amino acid derivative, and a di-acid derivative. Based upon these illustrative syntheses, several analogous derivatives can be synthesized with ease.

With reference to Reaction VI, above, 1,1'-carbonyldiimidazole (486 mg, 3.0 mmol) was first added to the corresponding carboxylic acid (3.0 mmol) in dimethylformamide (DMF) (8 mL) at 23° C. For the following examples only, $R^{10}$ of the acid and corresponding 3-substituted lapachone product can be $CH_2CH_2NHBoc$- (Boc=t-butoxycarbonyl) (22a), $CH_2CO_2C(CH_3)_2$- (22b), or methyl (22c).

After stirring for 20 minutes, 3-hydroxy-β-lapachone (19) (517 mg, 2.0 mmol) and DBU (389 uL, 26 mmol) were added to the mixture. (DBU=1,8-diazabicyclo (5.4.0)undec-7-ene, a relatively strong, sterically-hindered, non-nucleophilic base.) The mixture was stirred for 5 hours and poured into water (150 mL). The precipitate was collected by filtration and purified by silica gel chromatography (10–33% ethyl acetate in hexanes) to afford (22) (approximately 50% yield).

With reference to Reaction VII, compound (22a) (200 mg, 0.466 mmol) was added to diethyl ether (200 mL). A small amount of undissolved residue was removed by filtration. To the clear solution, hydrogen bromide (35% in acetic acid, 3.0 mL) was added at 23° C. After stirring for 10 minutes, the solution was filtered, and the precipitate re-crystallized from methanol to afford (23) (52 mg, 27%): ¹H NMR ($D_2O$, 300 MHz) δ 8.05–7.60 (m, 4H), 5.13 (m, 1H), 3.10 (t, J=6.5 Hz, 2H), 2.84–2.50 (M,4H), 1.39 (s, 3H), 1.31 (s, 3H).

Referring now to Reaction VIII, trifluoroacetic acid (1.0 mL) was added to a solution of compound (22b) (330 mg) in $CH_2Cl_2$ (1.5 mL) at 23° C. After stirring 1 hour the mixture was concentrated in vacuo. The residue was dissolved in MeO-t-Bu (50 mL) and extracted with saturated $NaHCO_3$ (2×25 mL). The combined aqueous layers were counter-extracted with diethyl ether and acidified with concentrated HCl. The resultant precipitate was filtered to give the malonyl derivative (24) (136 mg, 48%): ¹H NMR (CDCl₃, 300 MHz) δ 8.08 (d, J=7.6 Hz, 1H), 7.85 (d, J=7.8 Hz, 1H), 7.69 (t, J=7.6 Hz, 1H), 7.55 (t, J=7.5 Hz, 1H), 5.19 (t, J=4.6 Hz, 1H), 3.36 (s, 2H), 2.84 (dd, J=18.2, 4.9 Hz, 1H), 2.73 (dd, J=18.2, 4.4 Hz, 1H), 1.52 (s, 3H), 1.48 (s, 3H); ¹³C NMR (CDCl₃, 75 MHz) δ 179.43 (s), 178.64 (s), 170.12 (s), 161.22 (s), 134.98 (d), 132.07 (s), 131.08 (d), 130.21 (s), 128.93 (d), 124.37 (d), 110.12 (s), 79.76 (s), 69.11 (d), 24.98 (q), 23.29 (q), 22.71 (t), 21.02 (q); MS (FAB) m/z 136, 154, 241, 345 (MH⁺).

3-(n-Butyloxycarboxy-β-alanyloxy)-β-lapachone (22a): ¹H NMR (CDCl₃, 300 MHz) δ 8.10 (d, 1H), 7.84 (d, 1H), 7.67 (t, 1H), 7.54 (t, 1H), 5.17 (t, 1H), 3.53–3.32 (m, 1H), 2.93 (br, 1H), 2.85 (dd, 1H), 2.70 (dd, 1H), 2.65–2.50 (m, 1H), 1.47 (d, 6H), 1.42 (s, 9H).

3-(β-Alanyloxy)-β-lapachone (23): mp 228–229° C. (decomposed); ¹H NMR ($D_2O$, 300 MHz) δ 8.05–7.60 (m, 4H), 5.13 (m, 1H), 3.10 (t, J=6.5 Hz, 2H), 2.84–2.50 (m, 4H), 1.39 (s, 3H); ¹³C NMR ($D_2O$, 75 MHz, DMSO-d6 was added as internal standard) δ 181.77 (s), 180.84 (s), 173.02 (s), 165.13 (s), 137.45 (d), 132.93 (s), 130.79 (s), 130.03 (d), 126.34 (d), 110.92 (s), 82.29 (s), 71.99 (d), 36.34 (t), 32.57 (t), 25.41 (q), 24.10 (q), 23.35 (t); MS (FAB) m/z 122.0, 205.1, 241.1, 301.1, 330.1, (MH⁺), 659.1 (2M+H⁺).

3-(2'-t-Butyloxycarboxyacetoxy)-β-lapachone (22b) (27%): $^1$H NMR (CDCl$_3$, 300 MHz) δ 8.10 (d, 1H), 7.84 (d, 1H), 7.68 (t, 1H), 7.55 (t, 1H), 5.22 (t, 1H), 3.33 (s, 2H), 2.95 (dd, 1H), 2.74 (dd, 1H), 1.52 (d, 6H), 1.42 (s, 9H).

3-Acetoxy-β-lapachone (22c): $^1$H NMR (CDCl$_3$. 300 MHz) δ 8.09 (d, J=7.6 Hz, 1H), 7.85 (d, J=7.8 Hz, 1H), 7.68 (t, J=7.6 Hz, 1H), 7.55 (t, J=7.6 Hz, 1H), 5.15 (t, J=4.5 Hz, 1H), 2.82 (dd, J=18.2, 4.8 Hz, 1H), 2.68 (dd, J=18.2, 4.1 Hz, 1H), 2.08 (s, 3H), 1.49 (s, 3H), 1.44 (s, 3H); $^{13}$CNMR (CDCl$_3$, 75 MHz) δ 179.43 (s), 178.64 (s), 170.12 (s), 161.22 (s), 134.98 (d), 132.07 (s), 131.08 (d), 130.21 (s), 128.93 (d), 124.37 (d), 110.12 (s), 79.76 (s), 69.11 (d), 24.98 (q), 23.29 (q), 22.71 (t), 21.02 (q).

It is understood that the invention is not confined to the particular chemical reactions, reagents, solvents, transformations, or cell lines herein illustrated and described, but embraces all such modified forms thereof as come within the scope of the following claims.

What is claimed is:

1. A compound of Formula II:

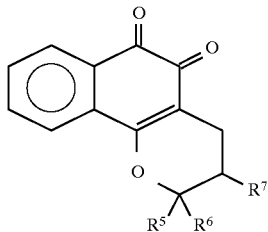

Formula II wherein $R^5$ and $R^6$ are each, independently, selected from the group consisting of H, $C_1$–$C_6$ alkyl, $C_1$–$C_6$ alkenyl, $C_1$–$C_6$ alkoxy, $C_1$–$C_6$ alkoxycarbonyl, —(CH$_2$)$_n$-aryl, and —(CH$_2$)$_n$-phenyl; and $R^7$ is selected from the group consisting of —(CH$_2$)$_n$-amino, β-alanyl, malonyl, —(CH$_2$)$_n$-aryl, and —(CH$_2$)$_n$-phenyl, and n is an integer of from 0 to 10, and salts thereof.

2. The compound according to claim 1, wherein the compound is selected from the group consisting of 3-(β-alanyl)-β-lapachone and 3-malonyl-β-lapachone.

3. A pharmaceutical unit dosage form comprising an amount of a compound of Formula II:

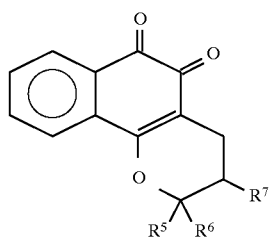

Formula II wherein $R^5$ and $R^6$ are each, independently, selected from the group consisting of H, $C_1$–$C_6$ alkyl, $C_1$–$C_6$ alkenyl, $C_1$–$C_6$ alkoxy, $C_1$–$C_6$ alkoxycarbonyl, —(CH$_2$)$_n$-aryl, and —(CH$_2$)$_n$-phenyl; and $R^7$ is selected from the group consisting of —(CH$_2$)$_n$-amino, β-alanyl, malonyl, —(CH$_2$)$_n$-aryl, and —(CH$_2$)$_n$-phenyl, and wherein n is an integer of from 0 to 10; pharmaceutically-suitable salts thereof, and combinations thereof; and wherein the amount is effective to inhibit growth of cancer cells in a human cancer patient following administration thereto.

4. The pharmaceutical unit dosage form of claim 3, comprising an amount of a compound selected from the group consisting of 3-(β-alanyl)-β-lapachone and 3-malonyl-β-lapachone, pharmaceutically-acceptable salts thereof, and combinations thereof.

5. The pharmaceutical unit dosage form of claim 4 in combination with a pharmaceutically-acceptable carrier.

6. The pharmaceutical unit dosage form of claim 5, wherein the carrier is a solid carrier.

7. The pharmaceutical unit dosage form of claim 5, wherein the carrier is a liquid carrier.

* * * * *